US007693698B2

(12) United States Patent
Mosyak et al.

(10) Patent No.: US 7,693,698 B2
(45) Date of Patent: Apr. 6, 2010

(54) METHOD FOR IDENTIFYING OR DESIGNING A CANDIDATE AGENT THAT INTERACTS WITH LINGO-1 POLYPEPTIDE USING A LINGO-1 THREE-DIMENSIONAL STRUCTURE

(75) Inventors: Lidia Mosyak, Newton Center, MA (US); Brian Dwyer, Dedham, MA (US); Mark Johnson, Bridgewater, MA (US); Xiaotian Zhong, Wayland, MA (US); Eleonora Presman, Stoughton, MA (US); James M. Wilhelm, Boston, MA (US); Mark Stahl, Lexington, MA (US); William Stuart Somers, Lexington, MA (US)

(73) Assignee: Wyeth LLC, Madison, NJ (US)

( * ) Notice: Subject to any disclaimer, the term of this patent is extended or adjusted under 35 U.S.C. 154(b) by 446 days.

(21) Appl. No.: 11/701,635

(22) Filed: Feb. 1, 2007

(65) Prior Publication Data
US 2007/0274918 A1 Nov. 29, 2007

Related U.S. Application Data

(60) Provisional application No. 60/765,443, filed on Feb. 3, 2006.

(51) Int. Cl.
*G06G 7/58* (2006.01)
*G01N 31/00* (2006.01)

(52) U.S. Cl. ............................................. 703/11; 436/4
(58) Field of Classification Search ...................... None
See application file for complete search history.

(56) References Cited

U.S. PATENT DOCUMENTS

| 5,834,228 A | 11/1998 | Becker et al. |
| 5,856,116 A | 1/1999 | Wilson et al. |
| 5,939,528 A | 8/1999 | Clardy et al. |

FOREIGN PATENT DOCUMENTS

WO       WO 99/09148        2/1999

OTHER PUBLICATIONS

Abrahams and Leslie, *Acta Cryst.*, D52:30-42 (1996).
Bell et al., *Trends Immunol.*, 24:528-533 (2003).
Brunger et al., "Crystallography & NMR System: A New Software Suite for Macromolecular Structure Determination," *Acta Crystallogr.*, D 54:905-921 (1997).
Carim-Todd et al., *Eur. J. Neurosci.*, 18(12):3167-3182 (2003).

(Continued)

*Primary Examiner*—David J Steadman
*Assistant Examiner*—Alexander D Kim
(74) *Attorney, Agent, or Firm*—Lando & Anastasi, LLP

(57) ABSTRACT

This disclosure relates to LINGO-1 polypeptides, LINGO-1 polypeptide/ligand complexes, crystals of LINGO-1 polypeptides, crystals of LINGO-1 polypeptide/ligand complexes, and related methods and software systems.

29 Claims, 12 Drawing Sheets

OTHER PUBLICATIONS

Collaborative Computational Project, No. 4, "The CCP4 Suite: Programs for Protein Crystallography," *Acta Crystallogr.*, D50:760-773 (1994).
Cowtan and Main, *Acta Cryst.*, D49:148-157 (1993).
De La Fortelle and Bricogne, *Meth. Enzym.*, 276:472-494 (1997).
Emsley and Cowtan, *Acta Cryst.* D60:2126-2132 (2004).
He et al., *Neuron*, 38:177-185 (2003).
Holyoak et al., *Biological Crystallography*, D59:2356-2358 (2003).
Huizinga et al., *Science*, 297:1176-1179 (2002).
McCoy et al., *Acta Cryst.*, D61:458-464 (2005).
Mi et al., *Nat. Neuroscience*, 8:745-751 (2005).
Mi et al., *Nature Neuroscience*, 7(3):221-228 (2004).
Mosyak et al., *J. Biol. Chem.* 281(47):36378-36390 (2006).
Murshudov et al., *Acta Crystallogr.*, D53:240-255 (1997).
Okafuji et al., *Gene Expr. Patterns*, 6(1):57-62 (2005).
Otwinowski and Minor, *Methods Enzymol.*, 276:307-326 (1997).
Rudd et al., *J. Mol. Biol.*, 293:351-366 (1999).
Soroka et al., *Structure*, 10:1291-1301 (2003).
Zhong et al., *Biochim. Biophys. Acta*, 1723:143-150 (2005).

```
1    TGCPPRCECS  AQDRAVLCHR  KRFVAVPEGI  PTETRLLDLG  KNRIKTLNQD  EFASFPHLEE
61   LELNENIVSA  VEPGAFNNLF  NLRTLGLRSN  RLKLIPLGVF  TGLSNLTKLD  ISENKIVILL
121  DYMFQDLYNL  KSLEVGDNDL  VYISHRAFSG  LNSLEQLTLE  KCNLTSIPTE  ALSHLHGLIV
181  LRLRHLNINA  IRDYSFKRLY  RLKVLEISHW  PYLDTMTPNC  LYGLNLTSLS  ITHCNLTAVP
241  YLAVRHLVYL  RFLNLSYNPI  STIEGSMLHE  LLRLQEIQLV  GGQLAVVEPY  AFRGLNYLRV
301  LNVSGNQLTT  LEESVFHSVG  NLETLILDSN  PLACDCRLLW  VFRRRWRLNF  NRQQPTCATP
361  EFVQGKEFKD  FPDVLLPNYF  TCRRARIRDR  KAQQVFVDEG  HTVQFVCRAD  GDPPPAILWL
421  SPRKHLVSAK  SNGRLTVFPD  GTLEVRYAQV  QDNGTYLCIA  ANAGGNDSMP  AHLHVRSYSP
481  DWPHQPNKTF  AFISNQPGEG  EANSTRATVP  FPFDIKHHHH  HH
```

SEQ ID NO:1

```
FEATURES             Location/Qualifiers
    rep_origin       5622..5943
                     /label=SV40
    promoter         1..540
                     /label=Murine\CMV
    promoter         5944..5949
                     /label=Murine\CMV
    misc_feature     550..690
                     /label=Tripartite\leader
    rep_origin       3378..5621
                     /label=Col\E1
    misc_signal      978..1524
                     /label=IRES\(EMCV)
    polyA_site       2776..3014
                     /label=SV40PolyA
    CDS              1544..2666
                     /label=GS
    misc_RNA         3020..3361
                     /label=VAI
BASE COUNT      1450 a      1532 c      1510 g      1457 t
ORIGIN
        1 tactgagtca ttagggactt tccaatgggt tttgcccagt acataaggtc aatagggdtg
       61 aatcaacagg aaagtcccat tggagccaag tacactgagt caatagggac tttccattgg
      121 gttttgccca gtacaaaagg tcaatagggg gtgagtcaat gggttttcc cattattggc
      181 acgtacataa ggtcaatagg ggtgagtcat gggttttc cagccaattt aattaaaacg
      241 ccatgtactt tcccaccatt gacgtcaatg gctattgaa actaatgcaa cgtgaccttt
      301 aaacggtact ttcccatagc tgattaatgg gaaagtaccg ttctcgagcc aatacacgtc
      361 aatgggaagt gaaagggcag ccaaaacgta acaccgcccc ggttttcccc tggaaattcc
      421 atattggcac gcattctatt ggctgagctg cgttctacgt gggtataaga ggcgcgacca
      481 gcgtcggtac cgtcgcagtc ttcggtctga ccaccgtaga acgcagagct cctcgctgca
      541 gcccaagctc tgttgggctc gcggttgagg acaaactctt cgcggtcttt ccagtactct
      601 tggatcggaa acccgtcggc ctccgaacgg tactccgcca ccgagggacc tgagcgagtc
```

FIG. 7A-2

```
 661 cgcatcgacc ggatcggaaa acctctcgac tgttggggtg agtactccct ctcaaaagcg
 721 ggcatgactt ctgcgctaag attgtcagtt tccaaaaacg aggaggattt gatattcacc
 781 tggcccgcgg tgatgccttt gagggtggcc gcgtccatct ggtcagaaaa gacaatcttt
 841 ttgttgtcaa gcttgaggtg tggcaggctt gagatctggc catacacttg agtgacaatg
 901 acatccactt tgcctttctc tccacaggtg tccactccca ggtccaactg caggtcgact
 961 ctagacccgg ggaattctaa cgttactggc cgaagccgct tggaataagg ccggtgtgcg
1021 tttgtctata tgttattttc caccatattg ccgtcttttg gcaatgtgag ggcccggaaa
1081 cctggccctg tcttcttgac gagcattcct aggggtcttt ccctctcgc caaaggaatg
1141 caaggtctgt tgaatgtcgt gaaggaagca gttcctctgg aagcttcttg aagacaaaca
1201 acgtctgtag cgacccttttg caggcagcgg aacccccac ctggcgacag gtgcctctgc
1261 ggccaaaagc cacgtgtata agatacacct gcaaggcgg cacaacccca gtgccacgtt
1321 gtgagttgga tagttgtgga aagagtcaaa tggctctcct caagcgtatt caacaagggg
1381 ctgaaggatg cccagaaggt accccattgt atgggatctg atctggggcc tcggtgcaca
1441 tgctttacat gtgtttagtc gaggttaaaa aacgtctagg ccccccgaac cacggggacg
1501 tggttttcct ttgaaaaaca cgattgctcg agttgccacc accatggcca cctcagcaag
1561 ttcccacttg aacaaaaaca tcaagcaaat gtacttgtgc ctgccccagg gtgagaaagt
1621 ccaagccatg tatatctggg ttgatggtac tggagaagga ctgcgctgca aacccgcac
1681 cctggactgt gagcccaagt gtgtagaaga gttacctgag tggaatttttg atggctctag
1741 tacctttcag tctgagggct ccaacagtga catgtatctc agccctgttg ccatgtttcg
1801 ggacccctttc cgcagagatc ccaacaagct ggtgttctgt gaagttttca agtacaaccg
1861 gaagcctgca gagaccaatt taaggcactc gtgtaaacgg ataatggaca tggtgagcaa
1921 ccagcacccc tggtttggaa tggaacagga gtatactctg atgggaacag atgggcaccc
1981 ttttggttgg ccttccaatg gctttcctgg gccccaaggt ccgtattact gtggtgtggg
2041 cgcagacaaa gcctatggca gggatatcgt ggaggctcac taccgcgcct gcttgtatgc
2101 tggggtcaag attacaggaa caaatgctga ggtcatgcct gcccagtggg agttccaaat
2161 aggaccctgt gaaggaatcc gcatgggaga tcatctctgg gtggcccgtt tcatcttgca
2221 tcgagtatgt gaagactttg ggtaatagc aacctttgac cccaagccca ttcctgggaa
2281 ctggaatggt gcaggctgcc ataccaactt tagcaccaag gccatgcggg aggagaatgg
2341 tctgaagcac atcgaggagg ccatcgagaa actaagcaag cggcaccggt accacattcg
2401 agcctacgat cccaagggg gcctggacaa tgcccgtcgt ctgactgggt tccacgaaac
2461 gtccaacatc aacgactttt ctgctggtgt cgccaatcgc agtgccagca tccgcattcc
2521 ccggactgtc ggccaggaga agaaaggtta ctttgaagac cgccgcccct ctgccaattg
2581 tgacccctttt gcagtgacag aagccatcgt ccgcacatgc cttctcaatg agactggcga
2641 cgagcccttc caatacaaaa actaattaga ctttgagtga tcttgagcct ttcctagttc
2701 atcccacccc gccccagaga gatctacgcg tatgcatttt ttataagacc atgggacttt
2761 tgctggcttt agatcataat cagccatacc acatttgtag aggttttact tgctttaaaa
2821 aacctcccac acctccccct gaacctgaaa cataaaatga atgcaattgt tgttgttaac
2881 ttgtttattg cagcttataa tggttacaaa taaagcaata gcatcacaaa tttcacaaat
2941 aaagcatttt tttcactgca ttctagttgt ggtttgtcca aactcatcaa tgtatcttat
3001 catgtctgga tccccggcca acggtctggt gacccggctg cgagagctcg gtgtacctga
3061 gacgcgagta agcccttgag tcaaagacgt agtcgttgca agtccgcacc aggtactgat
3121 catcgatgct agaccgtgca aaaggagagc ctgtaagcgg gcactcttcc gtggtctggt
3181 ggataaattc gcaagggtat catggcggac gaccggggtt cgaaccccgg atccggccgt
3241 ccgccgtgat ccatccggtt accgcccgcg tgtcgaaccc aggtgtgcga cgtcagacaa
3301 cgggggagcg ctcctttttgg cttccttcca ggcgcggcgg ctgctgcgct agcttttttg
3361 gcgagctcga attaattctg cattaatgaa tcggccaacg cgcggggaga ggcggtttgc
3421 gtattgggcg ctcttccgct tcctcgctca ctgactcgct gcgctcggtc gttcggctgc
3481 ggcgagcggt atcagctcac tcaaaggcgg taatacggtt atccacagaa tcagggggata
3541 acgcaggaaa gaacatgtga gcaaaaggcc agcaaaggc caggaaccgt aaaaaggccg
3601 cgttgctggc gttttccat aggctccgcc cccctgacga gcatcacaaa aatcgacgct
3661 caagtcagag gtggcgaaac ccgacaggac tataaagata ccaggcgttt cccccctggaa
```

FIG. 7A-3

```
3721 gctccctcgt gcgctctcct gttccgaccc tgccgcttac cggatacctg tccgcctttc
3781 tcccttcggg aagcgtggcg ctttctcaat gctcacgctg taggtatctc agttcggtgt
3841 aggtcgttcg ctccaagctg ggctgtgtgc acgaaccccc cgttcagccc gaccgctgcg
3901 ccttatccgg taactatcgt cttgagtcca acccggtaag cacgactta tcgccactgg
3961 cagcagccac tggtaacagg attagcagag cgaggtatgt aggcggtgct acagagttct
4021 tgaagtggtg gcctaactac ggctacacta gaaggacagt atttggtatc tgcgctctgc
4081 tgaagccagt taccttcgga aaaagagttg gtagctcttg atccggcaaa caaaccaccg
4141 ctggtagcgg tggttttttt gtttgcaagc agcagattac gcgcagaaaa aaggatctc
4201 aagaagatcc tttgatcttt tctacggggt ctgacgctca gtggaacgaa aactcacgtt
4261 aagggatttt ggtcatgaga ttatcaaaaa ggatcttcac ctagatcctt taaattaaa
4321 aatgaagttt taaatcaatc taaagtatat atgagtaaac ttggtctgac agttaccaat
4381 gcttaatcag tgaggcacct atctcagcga tctgtctatt tcgttcatcc atagttgcct
4441 gactccccgt cgtgtagata actacgatac gggagggctt accatctggc cccagtgctg
4501 caatgatacc gcgagaccca cgctcaccgg ctccagattt atcagcaata aaccagccag
4561 ccggaagggc cgagcgcaga agtggtcctg caactttatc cgcctccatc cagtctatta
4621 attgttgccg ggaagctaga gtaagtagtt cgccagttaa tagtttgcgc aacgttgttg
4681 ccattgctac aggcatcgtg gtgtcacgct cgtcgtttgg tatggcttca ttcagctccg
4741 gttcccaacg atcaaggcga gttacatgat cccccatgtt gtgcaaaaaa gcggttagct
4801 ccttcggtcc tccgatcgtt gtcagaagta agttggccgc agtgttatca ctcatggtta
4861 tggcagcact gcataattct cttactgtca tgccatccgt aagatgcttt tctgtgactg
4921 gtgagtactc aaccaagtca ttctgagaat agtgtatgcg gcgaccgagt tgctcttgcc
4981 cggcgtcaat acgggataat accgcgccac atagcagaac tttaaaagtg ctcatcattg
5041 gaaaacgttc ttcggggcga aaactctcaa ggatcttacc gctgttgaga tccagttcga
5101 tgtaacccac tcgtgcaccc aactgatctt cagcatcttt tactttcacc agcgtttctg
5161 ggtgagcaaa aacaggaagg caaaatgccg caaaaaaggg aataagggcg acacggaaat
5221 gttgaatact catactcttc cttttttcaat attattgaag catttatcag ggttattgtc
5281 tcatgagcgg atacatattt gaatgtattt agaaaaataa acaaataggg gttccgcgca
5341 catttccccg aaaagtgcca cctgacgtct aagaaaccat tattatcatg acattaacct
5401 ataaaaatag gcgtatcacg aggccctttc gtctcgcgcg tttcggtgat gacggtgaaa
5461 acctctgaca catgcagctc ccggagacgg tcacagcttg tctgtaagcg gatgccggga
5521 gcagacaagc ccgtcagggc gcgtcagcgg gtgttggcgg gtgtcggggc tggcttaact
5581 atgcggcatc agagcagatt gtactgagag tgcaccatat gtgtgtcagt tagggtgtgg
5641 aaagtcccca ggctcccag caggcagaag tatgcaaagc atgcatctca attagtcagc
5701 aaccaggtgt ggaaagtccc caggctcccc agcaggcaga agtatgcaaa gcatgcatct
5761 caattagtca gcaaccatag tcccgcccct aactccgccc atcccgcccc taactccgcc
5821 cagttccgcc cattctccgc cccatggctg actaattttt tttatttatg cagaggccga
5881 ggccgcctcg gcctctgagc tattccagaa gtagtgagga ggcttttttg gaggcctagg
5941 cttgtatac
```

(SEQ ID NO:2)

```
  1 mqvskrmlag gvrsmpspll acwqpilllv lgsvlsgsat gcpprcecsa qdravlchrk
 61 rfvavpegip tetrlldlgk nriktlnqde fasfphleel elnenivsav epgafnnlfn
121 lrtlglrsnr lkliplgvft glsnltkldi senkivilld ymfqdlynlk slevgdndlv
181 yishrafsgl nsleqltlek cnltsiptea lshlhglivl rlrhlninai rdysfkrlyr
241 lkvleishwp yldtmtpncl yglnltslsi thcnltavpy lavrhlvylr flnlsynpis
301 tiegsmlhel lrlqeiqlvg gqlavvepya frglnylrvl nvsgnqlttl eesvfhsvgn
361 letlildsnp lacdcrllwv frrrwrlnfn rqqptcatpe fvqgkefkdf pdvllpnyft
421 crrarirdrk aqqvfvdegh tvqfvcradg dpppailwls prkhlvsaks ngrltvfpdg
481 tlevryaqvq dngtylciaa naggndsmpa hlhvrsyspd wphqpnktfa fisnqpgege
541 anstratvpf pfdiktliia ttmgfisflg vvlfclvllf lwsrgkgntk hnieieyvpr
601 ksdagissad aprkfnmkmi (SEQ ID NO:3)
```

FIG. 8A

```
   1 ggagagacat gcgattggtg accgagccga gcggaccgaa ggcgcgcccg agatgcaggt
  61 gagcaagagg atgctggcgg ggggcgtgag gagcatgccc agccccctcc tggcctgctg
 121 gcagcccatc ctcctgctgg tgctgggctc agtgctgtca ggctcggcca cgggctgccc
 181 gccccgctgc gagtgctccg cccaggaccg cgctgtgctg tgccaccgca agcgctttgt
 241 ggcagtcccc gagggcatcc ccaccgagac gcgcctgctg gacctaggca agaaccgcat
 301 caaaacgctc aaccaggacg agttcgccag cttcccgcac ctggaggagc tggagctcaa
 361 cgagaacatc gtgagcgccg tggagcccgg cgccttcaac aacctcttca acctccggac
 421 gctgggtctc cgcagcaacc gcctgaagct catcccgcta ggcgtcttca ctggcctcag
 481 caacctgacc aagctggaca tcagcgagaa caagatcgtt atcctactgg actacatgtt
 541 tcaggacctg tacaacctca agtcactgga ggttggcgac aatgacctcg tctacatctc
 601 tcaccgcgcc ttcagcggcc tcaacagcct ggagcagctg acgctggaga aatgcaacct
 661 gacctccatc cccaccgagg cgctgtccca cctgcacggc ctcatcgtcc tgaggctccg
 721 gcacctcaac atcaatgcca tccgggacta ctccttcaag aggctgtacc gactcaaggt
 781 cttggagatc tcccactggc cctacttgga caccatgaca cccaactgcc tctacggcct
 841 caacctgacg tccctgtcca tcacacactg caatctgacc gctgtgccct acctggccgt
 901 ccgccaccta gtctatctcc gcttcctcaa cctctcctac aaccccatca gcaccattga
 961 gggctccatg ttgcatgagc tgctccggct gcaggagatc cagctggtgg gcgggcagct
1021 ggccgtggtg gagccctatg ccttccgcgg cctcaactac ctgcgcgtgc tcaatgtctc
1081 tggcaaccag ctgaccacac tggaggaatc agtcttccac tcggtgggca acctggagac
1141 actcatcctg gactccaacc cgctggcctg cgactgtcgg ctcctgtggg tgttccggcg
1201 ccgctggcgg ctcaacttca ccggcagca gcccacgtgc gccacgcccg agtttgtcca
1261 gggcaaggag ttcaaggact ccctgatgt gctactgccc aactacttca cctgccgccg
1321 cgcccgcatc cgggaccgca aggcccagca ggtgtttgtg gacgagggcc acacggtgca
1381 gtttgtgtgc cgggccgatg gcgacccgcc gcccgccatc tctggctct cacccgaaa
1441 gcacctggtc tcagccaaga gcaatgggcg gctcacagtc ttccctgatg gcacgctgga
1501 ggtgcgctac gcccaggtac aggacaacgg cacgtacctg tgcatcgcgg ccaacgcggg
1561 cggcaacgac tccatgcccg cccacctgca tgtgcgcagc tactcgcccg actggcccca
1621 tcagcccaac aagaccttcg ctttcatctc caaccagccg ggcgagggag aggccaacag
1681 cacccgcgcc actgtgcctt tcccccttcga catcaagacc ctcatcatcg ccaccaccat
1741 gggcttcatc tctttcctgg gcgtcgtcct cttctgcctg gtgctgctgt ttctctggag
1801 ccggggcaag ggcaacacaa agcacaacat cgagatcgag tatgtgcccc gaaagtcgga
1861 cgcaggcatc agctccgccg acgcgccccg caagttcaac atgaagatga tatgaggccg
1921 gggcgggggg cagggacccc cgggcggccg ggcaggggaa ggggcctggc cgccacctgc
1981 tcactctcca gtccttccca cctcctccct acccttctac acacgttctc tttctccctc
2041 ccgcctccgt cccctgctgc ccccgccag ccctcaccac ctgccctcct ctaccagga
2101 cctcagaagc ccagacctgg ggaccccacc tacacagggg cattgacaga ctggagttga
2161 aagccgacga accgacacgc ggcagagtca ataattcaat aaaaagtta cgaactttct
2221 ctgtaacttg ggtttcaata attatggatt tttatgaaaa cttgaaataa taaaaagaga
2281 aaaaaactat ttcctatagc tagtcggaat gcaaactttt gacgtcctga ttgctccagg
2341 gccctcttcc aactcagttt cttgttttc tcttcctcct cctcctcttc ttcctccttt
2401 ctcttctctt ccccagtggg gagggatcac tcaggaaaac aggaaggag gttccagccc
2461 cacccacctg cccaccccgc ccaggcacc atcaggagca ggctagggg caggcctggg
2521 cccagctccg gctggctttt tgcagggcg caggtggagg gacaggtct gccgatgggg
2581 gtgggagcct gtctgctggg ctgccaggcg gcaccactgc aaggggtggg agcctggctt
2641 gggtgtggct gagactctgg acagaggctg ggtcctcct ggggacagc acagtcagtg
2701 gagagagcca ggggctggag gtggggccca cccagcctc tggtcccagc tctgctgctc
2761 acttgctgtg tggcctcaag caggtcactg gcctctctgg gcctcagtct ccacatctgt
2821 acaaatggga acattacccc ctgccctgcc tacctcacag ggctgttgtg aggaattgat
2881 gagatgatgt atgtgaaaca ctttgtaacc tgtaaagcgc tgtgcacacg tg
(SEQ ID NO:4)
```

FIG. 8B

```
                          SEQUENCE LISTING

<160> NUMBER OF SEQ ID NOS: 9

<210> SEQ ID NO 1
<211> LENGTH: 522
<212> TYPE: PRT
<213> ORGANISM: Artificial Sequence
<220> FEATURE:
<223> OTHER INFORMATION: Synthetically generated peptide

<400> SEQUENCE: 1

Thr Gly Cys Pro Pro Arg Cys Glu Cys Ser Ala Gln Asp Arg Ala Val
 1               5                  10                  15

Leu Cys His Arg Lys Arg Phe Val Ala Val Pro Glu Gly Ile Pro Thr
                20                  25                  30

Glu Thr Arg Leu Leu Asp Leu Gly Lys Asn Arg Ile Lys Thr Leu Asn
            35                  40                  45

Gln Asp Glu Phe Ala Ser Phe Pro His Leu Glu Glu Leu Glu Leu Asn
        50                  55                  60

Glu Asn Ile Val Ser Ala Val Glu Pro Gly Ala Phe Asn Asn Leu Phe
 65                  70                  75                  80

Asn Leu Arg Thr Leu Gly Leu Arg Ser Asn Arg Leu Lys Leu Ile Pro
                85                  90                  95

Leu Gly Val Phe Thr Gly Leu Ser Asn Leu Thr Lys Leu Asp Ile Ser
            100                 105                 110

Glu Asn Lys Ile Val Ile Leu Leu Asp Tyr Met Phe Gln Asp Leu Tyr
        115                 120                 125

Asn Leu Lys Ser Leu Glu Val Gly Asp Asn Asp Leu Val Tyr Ile Ser
    130                 135                 140

His Arg Ala Phe Ser Gly Leu Asn Ser Leu Glu Gln Leu Thr Leu Glu
145                 150                 155                 160

Lys Cys Asn Leu Thr Ser Ile Pro Thr Glu Ala Leu Ser His Leu His
                165                 170                 175

Gly Leu Ile Val Leu Arg Leu Arg His Leu Asn Ile Asn Ala Ile Arg
            180                 185                 190

Asp Tyr Ser Phe Lys Arg Leu Tyr Arg Leu Lys Val Leu Glu Ile Ser
        195                 200                 205

His Trp Pro Tyr Leu Asp Thr Met Thr Pro Asn Cys Leu Tyr Gly Leu
    210                 215                 220

Asn Leu Thr Ser Leu Ser Ile Thr His Cys Asn Leu Thr Ala Val Pro
225                 230                 235                 240

Tyr Leu Ala Val Arg His Leu Val Tyr Leu Arg Phe Leu Asn Leu Ser
                245                 250                 255

Tyr Asn Pro Ile Ser Thr Ile Glu Gly Ser Met Leu His Glu Leu Leu
            260                 265                 270
```

```
Arg Leu Gln Glu Ile Gln Leu Val Gly Gly Gln Leu Ala Val Val Glu
            275                 280                 285

Pro Tyr Ala Phe Arg Gly Leu Asn Tyr Leu Arg Val Leu Asn Val Ser
        290                 295                 300

Gly Asn Gln Leu Thr Thr Leu Glu Glu Ser Val Phe His Ser Val Gly
305                 310                 315                 320

Asn Leu Glu Thr Leu Ile Leu Asp Ser Asn Pro Leu Ala Cys Asp Cys
                325                 330                 335

Arg Leu Leu Trp Val Phe Arg Arg Arg Trp Arg Leu Asn Phe Asn Arg
            340                 345                 350

Gln Gln Pro Thr Cys Ala Thr Pro Glu Phe Val Gln Gly Lys Glu Phe
        355                 360                 365

Lys Asp Phe Pro Asp Val Leu Leu Pro Asn Tyr Phe Thr Cys Arg Arg
370                 375                 380

Ala Arg Ile Arg Asp Arg Lys Ala Gln Gln Val Phe Val Asp Glu Gly
385                 390                 395                 400

His Thr Val Gln Phe Val Cys Arg Ala Asp Gly Asp Pro Pro Pro Ala
                405                 410                 415

Ile Leu Trp Leu Ser Pro Arg Lys His Leu Val Ser Ala Lys Ser Asn
            420                 425                 430

Gly Arg Leu Thr Val Phe Pro Asp Gly Thr Leu Glu Val Arg Tyr Ala
        435                 440                 445

Gln Val Gln Asp Asn Gly Thr Tyr Leu Cys Ile Ala Ala Asn Ala Gly
450                 455                 460

Gly Asn Asp Ser Met Pro Ala His Leu His Val Arg Ser Tyr Ser Pro
465                 470                 475                 480

Asp Trp Pro His Gln Pro Asn Lys Thr Phe Ala Phe Ile Ser Asn Gln
                485                 490                 495

Pro Gly Glu Gly Glu Ala Asn Ser Thr Arg Ala Thr Val Pro Phe Pro
            500                 505                 510

Phe Asp Ile Lys His His His His His His
            515                 520

<210> SEQ ID NO 2
<211> LENGTH: 5949
<212> TYPE: DNA
<213> ORGANISM: Artificial Sequence
<220> FEATURE:
<223> OTHER INFORMATION: Synthetic construct

<400> SEQUENCE: 2
tactgagtca ttagggactt tccaatgggt tttgcccagt acataaggtc aatagggttg      60
aatcaacagg aaagtcccat ggagccaagt acactgagtc aatagggac tttccattgg     120 gttttgccca gtacaaaagg tcaataggg gtgagtcaat gggttttttcc cattattggc     180 acgtacataa ggtcaatagg ggtgagtcat gggttttttc cagccaattt aattaaaacg     240
ccatgtactt tcccaccatt gacgtcaatg gctattgaa actaatgcaa cgtgaccttt     300
aaacggtact ttcccatagc tgattaatgg gaaagtaccg ttctcgagcc aatacacgtc     360
aatgggaagt gaaagggcag ccaaaacgta acaccgcccc ggttttcccc tggaaattcc     420
atattggcac gcattctatt ggctgagctg cgttctacgt gggtataaga ggcgcgacca     480
gcgtcggtac cgtcgcagtc ttcggtctga ccaccgtaga acgcagagct cctcgctgca     540
gcccaagctc tgtttgggct cgcggttgagg acaaactctt cgcggtcttt ccagtactct     600
tggatcggaa acccgtcggc ctccgaacgg tactccgcca ccgagggacc tgagcgagtc     660
```

```
cgcatcgacc ggatcggaaa acctctcgac tgttggggtg agtactccct ctcaaaagcg      720
ggcatgactt ctgcgctaag attgtcagtt tccaaaaacg aggaggattt gatattcacc      780
tggcccgcgg tgatgccttt gagggtggcc gcgtccatct ggtcagaaaa gacaatcttt      840
ttgttgtcaa gcttgaggtg tggcaggctt gagatctggc catacacttg agtgacaatg      900
acatccactt tgcctttctc tccacaggtg tccactccca ggtccaactg caggtcgact      960
ctagacccgg ggaattctaa cgttactggc cgaagccgct ggaataagg ccggtgtgcg      1020 tttgtctata tgttattttc caccatattg ccgtcttttg gcaatgtgag ggcccggaaa      1080
cctggccctg tcttcttgac gagcattcct aggggtcttt cccctctcgc caaggaatg       1140 caaggtctgt tgaatgtcgt gaaggaagca gttcctctgg aagcttcttg aagacaaaca      1200
acgtctgtag cgaccctttg caggcagcgg aaccccccac ctggcgacag gtgcctctgc      1260
ggccaaaagc cacgtgtata agatacacct gcaaaggcgg cacaacccca gtgccacgtt      1320
gtgagttgga tagttgtgga aagagtcaaa tggctctcct caagcgtatt caacaagggg      1380
ctgaaggatg cccagaaggt accccattgt atgggatctg atctggggcc tcggtgcaca      1440
tgctttacat gtgtttagtc gaggttaaaa aacgtctagg ccccccgaac cacggggacg      1500
tggttttcct ttgaaaaaca cgattgctcg agttgccacc accatggcca cctcagcaag      1560
ttcccacttg aacaaaaaca tcaagcaaat gtacttgtgc ctgccccagg gtgagaaagt      1620
ccaagccatg tatatctggg ttgatggtac tggagaagga ctgcgctgca aaacccgcac      1680
cctggactgt gagcccaagt gtgtagaaga gttacctgag tggaattttg atggctctag      1740
tacctttcag tctgagggct ccaacagtga catgtatctc agccctgttg ccatgtttcg      1800 ggacccettc cgcagagatc ccaacaagct ggtgttctgt gaagttttca gtacaaccg       1860 gaagcctgca gagaccaatt taaggcactc gtgtaaacgg ataatggaca tggtgagcaa      1920
ccagcacccc tggtttggaa tggaacagga gtatactctg atgggaacag atgggcaccc      1980
ttttggttgg ccttccaatg gctttcctgg gccccaaggt ccgtattact gtggtgtggg      2040
cgcagacaaa gcctatggca gggatatcgt ggaggctcac taccgcgcct gcttgtatgc      2100
tggggtcaag attacaggaa caaatgctga ggtcatgcct gcccagtggg agttccaaat      2160
aggaccctgt gaaggaatcc gcatgggaga tcatctctgg gtggcccgtt tcatcttgca      2220
tcgagtatgt gaagactttg gggtaatagc aacctttgac cccaagccca ttcctgggaa      2280
ctggaatggt gcaggctgcc ataccaactt tagcaccaag gccatgcggg aggagaatgg      2340
tctgaagcac atcgaggagg ccatcgagaa actaagcaag cggcaccggt accacattcg      2400
agcctacgat cccaaggggg gcctggacaa tgcccgtcgt ctgactgggt tccacgaaac      2460
gtccaacatc aacgactttt ctgctggtgt cgccaatcgc agtgccagca tccgcattcc      2520
ccggactgtc ggccaggaga agaaaggtta cttgaagac cgccgcccct ctgccaattg       2580 tgacccettt gcagtgacag aagccatcgt ccgcacatgc cttctcaatg agactggcga      2640
cgagcccttc caatacaaaa actaattaga ctttgagtga tcttgagcct ttcctagttc      2700
atccaccccc gccccagaga gatctacgcg tatgcatttt ttataagacc atgggacttt      2760
tgctggcttt agatcataat cagccatacc acatttgtag aggttttact tgctttaaaa      2820
aacctcccac acctcccct gaacctgaaa cataaaatga atgcaattgt tgttgttaac      2880
ttgtttattg cagcttataa tggttacaaa taaagcaata gcatcacaaa tttcacaaat      2940
aaagcatttt tttcactgca ttctagttgt ggtttgtcca aactcatcaa tgtatcttat      3000
catgtctgga tccccggcca acggtctggt gacccggctg cgagagctcg gtgtacctga     3060
```

```
gacgcgagta agcccttgag tcaaagacgt agtcgttgca agtccgcacc aggtactgat    3120
catcgatgct agaccgtgca aaaggagagc ctgtaagcgg gcactcttcc gtggtctggt    3180
ggataaattc gcaagggtat catggcggac gaccggggtt cgaacccgg atccggccgt     3240 ccgccgtgat ccatccggtt accgcccgcg tgtcgaaccc aggtgtgcga cgtcagacaa    3300
cgggggagcg ctccttttgg cttccttcca ggcgcggcgg ctgctgcgct agcttttttg    3360
gcgagctcga attaattctg cattaatgaa tcggccaacg cgcggggaga ggcggtttgc    3420
gtattgggcg ctcttccgct tcctcgctca ctgactcgct gcgctcggtc gttcggctgc    3480
ggcgagcggt atcagctcac tcaaaggcgg taatacggtt atccacagaa tcaggggata    3540
acgcaggaaa gaacatgtga gcaaaaggcc agcaaaaggc caggaaccgt aaaaaggccg    3600
cgttgctggc gtttttccat aggctccgcc cccctgacga gcatcacaaa aatcgacgct    3660
caagtcagag gtggcgaaac ccgacaggac tataaagata ccaggcgttt ccccctggaa    3720 gctcccctcgt gcgctctcct gttccgaccc tgccgcttac cggatacctg tccgcctttc    3780
tcccttcggg aagcgtggcg ctttctcaat gctcacgctg taggtatctc agttcggtgt    3840
aggtcgttcg ctccaagctg ggctgtgtgc acgaacccc cgttcagccc gaccgctgcg     3900
ccttatccgg taactatcgt cttgagtcca acccggtaag acacgactta tcgccactgg    3960
cagcagccac tggtaacagg attagcagag cgaggtatgt aggcggtgct acagagttct    4020
tgaagtggtg gcctaactac ggctacacta aaggacagt atttggtatc tgcgctctgc     4080
tgaagccagt taccttcgga aaagagttg gtagctcttg atccggcaaa caaaccaccg     4140
ctggtagcgg tggtttttttt gtttgcaagc agcagattac gcgcagaaaa aaaggatctc    4200
aagaagatcc tttgatcttt tctacggggt ctgacgctca gtggaacgaa aactcacgtt    4260
aagggatttt ggtcatgaga ttatcaaaaa ggatcttcac ctagatcctt ttaaattaaa    4320
aatgaagttt taaatcaatc taagtatat atgagtaaac ttggtctgac agttaccaat     4380
gcttaatcag tgaggcacct atctcagcga tctgtctatt tcgttcatcc atagttgcct    4440
gactccccgt cgtgtagata actacgatac gggagggctt accatctggc cccagtgctg    4500
caatgatacc gcgagaccca cgctcaccgg ctccagattt atcagcaata aaccagccag    4560
ccggaagggc cgagcgcaga agtggtcctg caactttatc cgcctccatc cagtctatta    4620
attgttgccg ggaagctaga gtaagtagtt cgccagttaa tagtttgcgc aacgttgttg    4680
ccattgctac aggcatcgtg gtgtcacgct cgtcgtttgg tatggcttca ttcagctccg    4740
gttcccaacg atcaaggcga gttacatgat cccccatgtt gtgcaaaaaa gcggttagct    4800
ccttcggtcc tccgatcgtt gtcagaagta agttggccgc agtgttatca ctcatggtta    4860
tggcagcact gcataattct cttactgtca tgccatccgt aagatgcttt tctgtgactg    4920
gtgagtactc aaccaagtca ttctgagaat agtgtatgcg gcgaccgagt tgctcttgcc    4980
cggcgtcaat acgggataat accgcgccac atagcagaac tttaaaagtg ctcatcattg    5040
gaaaacgttc ttcggggcga aaactctcaa ggatcttacc gctgttgaga tccagttcga    5100
tgtaacccac tcgtgcaccc aactgatctt cagcatcttt tactttcacc agcgtttctg    5160
ggtgagcaaa aacaggaagg caaaatgccg caaaaaaggg aataaggcg acacggaaat     5220 gttgaatact catactcttc cttttcaat attattgaag catttatcag ggttattgtc     5280
tcatgagcgg atacatattt gaatgtattt agaaaaataa acaaataggg gttccgcgca    5340
catttccccg aaaagtgcca cctgacgtct aagaaaccat tattatcatg acattaacct    5400
ataaaaatag gcgtatcacg aggcccttc gtctcgcgcg tttcggtgat gacggtgaaa     5460
```

-continued

```
acctctgaca catgcagctc ccggagacgg tcacagcttg tctgtaagcg gatgccggga    5520
gcagacaagc ccgtcagggc gcgtcagcgg gtgttggcgg gtgtcggggc tggcttaact    5580
atgcggcatc agagcagatt gtactgagag tgcaccatat gtgtgtcagt tagggtgtgg    5640
aaagtcccca ggctccccag caggcagaag tatgcaaagc atgcatctca attagtcagc    5700
aaccaggtgt ggaaagtccc caggctcccc agcaggcaga agtatgcaaa gcatgcatct    5760
caattagtca gcaaccatag tcccgcccct aactccgccc atcccgcccc taactccgcc    5820
cagttccgcc cattctccgc cccatggctg actaatttt tttatttatg cagaggccga    5880
ggccgcctcg gcctctgagc tattccagaa gtagtgagga ggcttttttg gaggcctagg    5940
cttgtatac                                                              5949
```

<210> SEQ ID NO 3
<211> LENGTH: 620
<212> TYPE: PRT
<213> ORGANISM: Homo sapiens

<400> SEQUENCE: 3

```
Met Gln Val Ser Lys Arg Met Leu Ala Gly Gly Val Arg Ser Met Pro
  1               5                  10                  15

Ser Pro Leu Leu Ala Cys Trp Gln Pro Ile Leu Leu Val Leu Leu Gly
                 20                  25                  30

Ser Val Leu Ser Gly Ser Ala Thr Gly Cys Pro Pro Arg Cys Glu Cys
             35                  40                  45

Ser Ala Gln Asp Arg Ala Val Leu Cys His Arg Lys Arg Phe Val Ala
         50                  55                  60

Val Pro Glu Gly Ile Pro Thr Glu Thr Arg Leu Leu Asp Leu Gly Lys
 65                  70                  75                  80

Asn Arg Ile Lys Thr Leu Asn Gln Asp Glu Phe Ala Ser Phe Pro His
                 85                  90                  95

Leu Glu Glu Leu Glu Leu Asn Glu Asn Ile Val Ser Ala Val Glu Pro
                100                 105                 110

Gly Ala Phe Asn Asn Leu Phe Asn Leu Arg Thr Leu Gly Leu Arg Ser
            115                 120                 125

Asn Arg Leu Lys Leu Ile Pro Leu Gly Val Phe Thr Gly Leu Ser Asn
        130                 135                 140

Leu Thr Lys Leu Asp Ile Ser Glu Asn Lys Ile Val Ile Leu Leu Asp
145                 150                 155                 160

Tyr Met Phe Gln Asp Leu Tyr Asn Leu Lys Ser Leu Glu Val Gly Asp
                165                 170                 175

Asn Asp Leu Val Tyr Ile Ser His Arg Ala Phe Ser Gly Leu Asn Ser
            180                 185                 190

Leu Glu Gln Leu Thr Leu Glu Lys Cys Asn Leu Thr Ser Ile Pro Thr
        195                 200                 205

Glu Ala Leu Ser His Leu His Gly Leu Ile Val Leu Arg Leu Arg His
    210                 215                 220

Leu Asn Ile Asn Ala Ile Arg Asp Tyr Ser Phe Lys Arg Leu Tyr Arg
225                 230                 235                 240

Leu Lys Val Leu Glu Ile Ser His Trp Pro Tyr Leu Asp Thr Met Thr
                245                 250                 255

Pro Asn Cys Leu Tyr Gly Leu Asn Leu Thr Ser Leu Ser Ile Thr His
            260                 265                 270

Cys Asn Leu Thr Ala Val Pro Tyr Leu Ala Val Arg His Leu Val Tyr
        275                 280                 285
```

```
Leu Arg Phe Leu Asn Leu Ser Tyr Asn Pro Ile Ser Thr Ile Glu Gly
    290                 295                 300
Ser Met Leu His Glu Leu Arg Leu Gln Glu Ile Gln Leu Val Gly
305                 310                 315                 320
Gly Gln Leu Ala Val Val Glu Pro Tyr Ala Phe Arg Gly Leu Asn Tyr
                325                 330                 335
Leu Arg Val Leu Asn Val Ser Gly Asn Gln Leu Thr Thr Leu Glu Glu
            340                 345                 350
Ser Val Phe His Ser Val Gly Asn Leu Glu Thr Leu Ile Leu Asp Ser
        355                 360                 365
Asn Pro Leu Ala Cys Asp Cys Arg Leu Leu Trp Val Phe Arg Arg Arg
370                 375                 380
Trp Arg Leu Asn Phe Asn Arg Gln Gln Pro Thr Cys Ala Thr Pro Glu
385                 390                 395                 400
Phe Val Gln Gly Lys Glu Phe Lys Asp Phe Pro Asp Val Leu Leu Pro
                405                 410                 415
Asn Tyr Phe Thr Cys Arg Arg Ala Arg Ile Arg Asp Arg Lys Ala Gln
            420                 425                 430
Gln Val Phe Val Asp Glu Gly His Thr Val Gln Phe Val Cys Arg Ala
        435                 440                 445
Asp Gly Asp Pro Pro Ala Ile Leu Trp Leu Ser Pro Arg Lys His
450                 455                 460
Leu Val Ser Ala Lys Ser Asn Gly Arg Leu Thr Val Phe Pro Asp Gly
465                 470                 475                 480
Thr Leu Glu Val Arg Tyr Ala Gln Val Gln Asp Asn Gly Thr Tyr Leu
                485                 490                 495
Cys Ile Ala Ala Asn Ala Gly Gly Asn Asp Ser Met Pro Ala His Leu
            500                 505                 510
His Val Arg Ser Tyr Ser Pro Asp Trp Pro His Gln Pro Asn Lys Thr
        515                 520                 525
Phe Ala Phe Ile Ser Asn Gln Pro Gly Glu Gly Glu Ala Asn Ser Thr
530                 535                 540
Arg Ala Thr Val Pro Phe Pro Phe Asp Ile Lys Thr Leu Ile Ile Ala
545                 550                 555                 560
Thr Thr Met Gly Phe Ile Ser Phe Leu Gly Val Val Leu Phe Cys Leu
                565                 570                 575
Val Leu Leu Phe Leu Trp Ser Arg Gly Lys Gly Asn Thr Lys His Asn
            580                 585                 590
Ile Glu Ile Glu Tyr Val Pro Arg Lys Ser Asp Ala Gly Ile Ser Ser
        595                 600                 605
Ala Asp Ala Pro Arg Lys Phe Asn Met Lys Met Ile
610                 615                 620

<210> SEQ ID NO 4
<211> LENGTH: 2932
<212> TYPE: DNA
<213> ORGANISM: Homo sapiens

<400> SEQUENCE: 4
ggagagacat gcgattggtg accgagccga gcggaccgaa ggcgcgcccg agatgcaggt      60
gagcaagagg atgctggcgg ggggcgtgag gagcatgccc agccccctcc tggcctgctg     120
gcagcccatc ctcctgctgg tgctgggctc agtgctgtca ggctcggcca cgggctgccc     180
gccccgctgc gagtgctccc cccaggaccg cgctgtgctg tgccaccgca agcgctttgt     240
```

-continued

```
ggcagtcccc gagggcatcc ccaccgagac gcgcctgctg gacctaggca agaaccgcat    300
caaaacgctc aaccaggacg agttcgccag cttcccgcac ctggaggagc tggagctcaa    360
cgagaacatc gtgagcgccg tggagcccgg cgccttcaac aacctcttca acctccggac    420
gctgggtctc cgcagcaacc gcctgaagct catcccgcta ggcgtcttca ctggcctcag    480
caacctgacc aagctggaca tcagcgagaa caagatcgtt atcctactgg actacatgtt    540
tcaggacctg tacaacctca agtcactgga ggttggcgac aatgacctcg tctacatctc    600
tcaccgcgcc ttcagcggcc tcaacagcct ggagcagctg acgctggaga atgcaacct    660 gacctccatc cccaccgagg cgctgtccca cctgcacggc ctcatcgtcc tgaggctccg    720
gcacctcaac atcaatgcca tccgggacta ctccttcaag aggctgtacc gactcaaggt    780
cttggagatc tcccactggc cctacttgga caccatgaca cccaactgcc tctacggcct    840
caacctgacg tccctgtcca tcacacactg caatctgacc gctgtgccct acctggccgt    900
ccgccaccta gtctatctcc gcttcctcaa cctctcctac aacccatca gcaccattga    960 gggctccatg ttgcatgagc tgctccggct gcaggagatc cagctggtgg gcgggcagct    1020
ggccgtggtg gagccctatg ccttccgcgg cctcaactac ctgcgcgtgc tcaatgtctc    1080
tggcaaccag ctgaccacac tggaggaatc agtcttccac tcggtgggca acctggagac    1140
actcatcctg gactccaacc gctggcctg cgactgtcgg ctcctgtggg tgttccggcg    1200
ccgctggcgg ctcaacttca accggcagca gcccacgtgc gccacgcccg agtttgtcca    1260
gggcaaggag ttcaaggact tccctgatgt gctactgccc aactacttca cctgccgccg    1320
cgcccgcatc cgggaccgca aagcccagca ggtgttttgtg gacgagggcc acacggtgca    1380
gtttgtgtgc cgggccgatg gcgacccgcc gcccgccatc ctctggctct cacccccgaaa    1440 gcacctggtc tcagccaaga gcaatgggcg gctcacagtc ttccctgatg gcacgctgga    1500
ggtgcgctac gcccaggtac aggacaacgg cacgtacctg tgcatcgcgg ccaacgcggg    1560
cggcaacgac tccatgcccg cccacctgca tgtgcgcagc tactcgcccg actggcccca    1620
tcagcccaac aagaccttcg ctttcatctc caaccagccg ggcgagggag aggccaacag    1680
cacccgcgcc actgtgcctt tccccttcga catcaagacc ctcatcatcg ccaccaccat    1740
gggcttcatc tctttcctgg gcgtcgtcct cttctgcctg gtgctgctgt ttctctggag    1800
ccggggcaag ggcaacacaa agcacaacat cgagatcgag tatgtgcccc gaaagtcgga    1860
cgcaggcatc agctccgccg acgcgccccg caagttcaac atgaagatga tatgaggccg    1920
gggcgggggg cagggacccc cggcggccg ggcaggggaa ggggcctggc cgccacctgc    1980
tcactctcca gtccttccca cctcctccct accttctac acacgttctc tttctccctc    2040
ccgcctccgt ccctgctgc ccccgccag ccctcaccac ctgccctcct tctaccagga    2100
cctcagaagc ccagacctgg ggaccccacc tacacagggg cattgacaga ctggagttga    2160
aagccgacga accgacacgc ggcagagtca ataattcaat aaaaaagtta cgaactttct    2220
ctgtaacttg ggtttcaata attatggatt tttatgaaaa cttgaaataa taaaaagaga    2280
aaaaaactat ttcctatagc tagtcggaat gcaaactttt gacgtcctga ttgctccagg    2340
gccctcttcc aactcagttt cttgtttttc tcttcctcct cctcctcttc ttcctccttt    2400
ctcttctctt cccagtgggg agggatcac tcaggaaaac aggaaaggag gttccagccc    2460
cacccacctg cccaccccgc cccaggcacc atcaggagca ggctagggg caggcctggg    2520 cccagctccg ggctggcttt ttgcaggggcg caggtggagg ggacaggtct gccgatgggg    2580
gtgggagcct gtctgctggg ctgccaggcg gcaccactgc aaggggtggg agcctggctt    2640
```

-continued

```
gggtgtggct gagactctgg acagaggctg gggtcctcct gggggacagc acagtcagtg    2700
gagagagcca ggggctggag gtggggccca ccccagcctc tggtcccagc tctgctgctg    2760
acttgctgtg tggcctcaag caggtcactg gcctctctgg gcctcagtct ccacatctgt    2820
acaaatggga acattacccc ctgccctgcc tacctcacag ggctgttgtg aggaattgat    2880
gagatgatgt atgtgaaaca ctttgtaacc tgtaaagcgc tgtgcacacg tg            2932
```

<210> SEQ ID NO 5
<211> LENGTH: 477
<212> TYPE: PRT
<213> ORGANISM: Homo sapiens

<400> SEQUENCE: 5

```
Thr Gly Cys Pro Pro Arg Cys Glu Cys Ser Ala Gln Asp Arg Ala Val
 1               5                  10                  15

Leu Cys His Arg Lys Arg Phe Val Ala Val Pro Glu Gly Ile Pro Thr
                20                  25                  30

Glu Thr Arg Leu Leu Asp Leu Gly Lys Asn Arg Ile Lys Thr Leu Asn
            35                  40                  45

Gln Asp Glu Phe Ala Ser Phe Pro His Leu Glu Leu Glu Leu Asn
        50                  55                  60

Glu Asn Ile Val Ser Ala Val Glu Pro Gly Ala Phe Asn Asn Leu Phe
 65                  70                  75                  80

Asn Leu Arg Thr Leu Gly Leu Arg Ser Asn Arg Leu Lys Leu Ile Pro
                85                  90                  95

Leu Gly Val Phe Thr Gly Leu Ser Asn Leu Thr Lys Leu Asp Ile Ser
            100                 105                 110

Glu Asn Lys Ile Val Ile Leu Leu Asp Tyr Met Phe Gln Asp Leu Tyr
        115                 120                 125

Asn Leu Lys Ser Leu Glu Val Gly Asp Asn Asp Leu Val Tyr Ile Ser
    130                 135                 140

His Arg Ala Phe Ser Gly Leu Asn Ser Leu Glu Gln Leu Thr Leu Glu
145                 150                 155                 160

Lys Cys Asn Leu Thr Ser Ile Pro Thr Glu Ala Leu Ser His Leu His
                165                 170                 175

Gly Leu Ile Val Leu Arg Leu Arg His Leu Asn Ile Asn Ala Ile Arg
            180                 185                 190

Asp Tyr Ser Phe Lys Arg Leu Tyr Arg Leu Lys Val Leu Glu Ile Ser
        195                 200                 205

His Trp Pro Tyr Leu Asp Thr Met Thr Pro Asn Cys Leu Tyr Gly Leu
    210                 215                 220

Asn Leu Thr Ser Leu Ser Ile Thr His Cys Asn Leu Thr Ala Val Pro
225                 230                 235                 240

Tyr Leu Ala Val Arg His Leu Val Tyr Leu Arg Phe Leu Asn Leu Ser
                245                 250                 255

Tyr Asn Pro Ile Ser Thr Ile Glu Gly Ser Met Leu His Glu Leu Leu
            260                 265                 270

Arg Leu Gln Glu Ile Gln Leu Val Gly Gly Gln Leu Ala Val Val Glu
        275                 280                 285

Pro Tyr Ala Phe Arg Gly Leu Asn Tyr Leu Arg Val Leu Asn Val Ser
    290                 295                 300

Gly Asn Gln Leu Thr Thr Leu Glu Glu Ser Val Phe His Ser Val Gly
305                 310                 315                 320
```

```
Asn Leu Glu Thr Leu Ile Leu Asp Ser Asn Pro Leu Ala Cys Asp Cys
                325                 330                 335

Arg Leu Leu Trp Val Phe Arg Arg Trp Arg Leu Asn Phe Asn Arg
                340                 345                 350

Gln Gln Pro Thr Cys Ala Thr Pro Glu Phe Val Gln Gly Lys Glu Phe
                355                 360                 365

Lys Asp Phe Pro Asp Val Leu Leu Pro Asn Tyr Phe Thr Cys Arg Arg
        370                 375                 380

Ala Arg Ile Arg Asp Arg Lys Ala Gln Gln Val Phe Val Asp Glu Gly
385                 390                 395                 400

His Thr Val Gln Phe Val Cys Arg Ala Asp Gly Asp Pro Pro Pro Ala
                405                 410                 415

Ile Leu Trp Leu Ser Pro Arg Lys His Leu Val Ser Ala Lys Ser Asn
                420                 425                 430

Gly Arg Leu Thr Val Phe Pro Asp Gly Thr Leu Glu Val Arg Tyr Ala
                435                 440                 445

Gln Val Gln Asp Asn Gly Thr Tyr Leu Cys Ile Ala Ala Asn Ala Gly
        450                 455                 460

Gly Asn Asp Ser Met Pro Ala His Leu His Val Arg Ser
465                 470                 475

<210> SEQ ID NO 6
<211> LENGTH: 473
<212> TYPE: PRT
<213> ORGANISM: Homo sapiens

<400> SEQUENCE: 6

Cys Pro Pro Arg Cys Glu Cys Ser Ala Gln Asp Arg Ala Val Leu Cys
1               5                   10                  15

His Arg Lys Arg Phe Val Ala Val Pro Glu Gly Ile Pro Thr Glu Thr
                20                  25                  30

Arg Leu Leu Asp Leu Gly Lys Asn Arg Ile Lys Thr Leu Asn Gln Asp
            35                  40                  45

Glu Phe Ala Ser Phe Pro His Leu Glu Glu Leu Glu Leu Asn Glu Asn
        50                  55                  60

Ile Val Ser Ala Val Glu Pro Gly Ala Phe Asn Asn Leu Phe Asn Leu
65              70                  75                  80

Arg Thr Leu Gly Leu Arg Ser Asn Arg Leu Lys Leu Ile Pro Leu Gly
                85                  90                  95

Val Phe Thr Gly Leu Ser Asn Leu Thr Lys Leu Asp Ile Ser Glu Asn
                100                 105                 110

Lys Ile Val Ile Leu Leu Asp Tyr Met Phe Gln Asp Leu Tyr Asn Leu
            115                 120                 125

Lys Ser Leu Glu Val Gly Asp Asn Asp Leu Val Tyr Ile Ser His Arg
        130                 135                 140

Ala Phe Ser Gly Leu Asn Ser Leu Glu Gln Leu Thr Leu Glu Lys Cys
145                 150                 155                 160

Asn Leu Thr Ser Ile Pro Thr Glu Ala Leu Ser His Leu His Gly Leu
                165                 170                 175

Ile Val Leu Arg Leu Arg His Leu Asn Ile Asn Ala Ile Arg Asp Tyr
                180                 185                 190

Ser Phe Lys Arg Leu Tyr Arg Leu Lys Val Leu Glu Ile Ser His Trp
            195                 200                 205

Pro Tyr Leu Asp Thr Met Thr Pro Asn Cys Leu Tyr Gly Leu Asn Leu
        210                 215                 220
```

```
Thr Ser Leu Ser Ile Thr His Cys Asn Leu Thr Ala Val Pro Tyr Leu
225                 230                 235                 240

Ala Val Arg His Leu Val Tyr Leu Arg Phe Leu Asn Leu Ser Tyr Asn
            245                 250                 255

Pro Ile Ser Thr Ile Glu Gly Ser Met Leu His Glu Leu Leu Arg Leu
        260                 265                 270

Gln Glu Ile Gln Leu Val Gly Gly Gln Leu Ala Val Val Glu Pro Tyr
    275                 280                 285

Ala Phe Arg Gly Leu Asn Tyr Leu Arg Val Leu Asn Val Ser Gly Asn
290                 295                 300

Gln Leu Thr Thr Leu Glu Glu Ser Val Phe His Ser Val Gly Asn Leu
305                 310                 315                 320

Glu Thr Leu Ile Leu Asp Ser Asn Pro Leu Ala Cys Asp Cys Arg Leu
            325                 330                 335

Leu Trp Val Phe Arg Arg Arg Trp Arg Leu Asn Phe Asn Arg Gln Gln
        340                 345                 350

Pro Thr Cys Ala Thr Pro Glu Phe Val Gln Gly Lys Glu Phe Lys Asp
    355                 360                 365

Phe Pro Asp Val Leu Leu Pro Asn Tyr Phe Thr Cys Arg Arg Ala Arg
370                 375                 380

Ile Arg Asp Arg Lys Ala Gln Gln Val Phe Val Asp Glu Gly His Thr
385                 390                 395                 400

Val Gln Phe Val Cys Arg Ala Asp Gly Asp Pro Pro Pro Ala Ile Leu
            405                 410                 415

Trp Leu Ser Pro Arg Lys His Leu Val Ser Ala Lys Ser Asn Gly Arg
        420                 425                 430

Leu Thr Val Phe Pro Asp Gly Thr Leu Glu Val Arg Tyr Ala Gln Val
    435                 440                 445

Gln Asp Asn Gly Thr Tyr Leu Cys Ile Ala Ala Asn Ala Gly Gly Asn
450                 455                 460

Asp Ser Met Pro Ala His Leu His Val
465                 470

<210> SEQ ID NO 7
<211> LENGTH: 476
<212> TYPE: PRT
<213> ORGANISM: Homo sapiens

<400> SEQUENCE: 7

Gly Cys Pro Pro Arg Cys Glu Cys Ser Ala Gln Asp Arg Ala Val Leu
1               5                   10                  15

Cys His Arg Lys Arg Phe Val Ala Val Pro Glu Gly Ile Pro Thr Glu
            20                  25                  30

Thr Arg Leu Leu Asp Leu Gly Lys Asn Arg Ile Lys Thr Leu Asn Gln
        35                  40                  45

Asp Glu Phe Ala Ser Phe Pro His Leu Glu Glu Leu Glu Leu Asn Glu
    50                  55                  60

Asn Ile Val Ser Ala Val Glu Pro Gly Ala Phe Asn Asn Leu Phe Asn
65                  70                  75                  80

Leu Arg Thr Leu Gly Leu Arg Ser Asn Arg Leu Lys Leu Ile Pro Leu
                85                  90                  95

Gly Val Phe Thr Gly Leu Ser Asn Leu Thr Lys Leu Asp Ile Ser Glu
            100                 105                 110

Asn Lys Ile Val Ile Leu Leu Asp Tyr Met Phe Gln Asp Leu Tyr Asn
        115                 120                 125
```

```
Leu Lys Ser Leu Glu Val Gly Asp Asn Asp Leu Val Tyr Ile Ser His
    130                 135                 140

Arg Ala Phe Ser Gly Leu Asn Ser Leu Glu Gln Leu Thr Leu Glu Lys
145                 150                 155                 160

Cys Asn Leu Thr Ser Ile Pro Thr Glu Ala Leu Ser His Leu His Gly
                165                 170                 175

Leu Ile Val Leu Arg Leu Arg His Leu Asn Ile Asn Ala Ile Arg Asp
            180                 185                 190

Tyr Ser Phe Lys Arg Leu Tyr Arg Leu Lys Val Leu Glu Ile Ser His
        195                 200                 205

Trp Pro Tyr Leu Asp Thr Met Thr Pro Asn Cys Leu Tyr Gly Leu Asn
    210                 215                 220

Leu Thr Ser Leu Ser Ile Thr His Cys Asn Leu Thr Ala Val Pro Tyr
225                 230                 235                 240

Leu Ala Val Arg His Leu Val Tyr Leu Arg Phe Leu Asn Leu Ser Tyr
                245                 250                 255

Asn Pro Ile Ser Thr Ile Glu Gly Ser Met Leu His Glu Leu Leu Arg
            260                 265                 270

Leu Gln Glu Ile Gln Leu Val Gly Gly Gln Leu Ala Val Val Glu Pro
        275                 280                 285

Tyr Ala Phe Arg Gly Leu Asn Tyr Leu Arg Val Leu Asn Val Ser Gly
    290                 295                 300

Asn Gln Leu Thr Thr Leu Glu Glu Ser Val Phe His Ser Val Gly Asn
305                 310                 315                 320

Leu Glu Thr Leu Ile Leu Asp Ser Asn Pro Leu Ala Cys Asp Cys Arg
                325                 330                 335

Leu Leu Trp Val Phe Arg Arg Arg Trp Arg Leu Asn Phe Asn Arg Gln
            340                 345                 350

Gln Pro Thr Cys Ala Thr Pro Glu Phe Val Gln Gly Lys Glu Phe Lys
        355                 360                 365

Asp Phe Pro Asp Val Leu Leu Pro Asn Tyr Phe Thr Cys Arg Arg Ala
    370                 375                 380

Arg Ile Arg Asp Arg Lys Ala Gln Gln Val Phe Val Asp Glu Gly His
385                 390                 395                 400

Thr Val Gln Phe Val Cys Arg Ala Asp Gly Asp Pro Pro Pro Ala Ile
                405                 410                 415

Leu Trp Leu Ser Pro Arg Lys His Leu Val Ser Ala Lys Ser Asn Gly
            420                 425                 430

Arg Leu Thr Val Phe Pro Asp Gly Thr Leu Glu Val Arg Tyr Ala Gln
        435                 440                 445

Val Gln Asp Asn Gly Thr Tyr Leu Cys Ile Ala Ala Asn Ala Gly Gly
    450                 455                 460

Asn Asp Ser Met Pro Ala His Leu His Val Arg Ser
465                 470                 475

<210> SEQ ID NO 8
<211> LENGTH: 474
<212> TYPE: PRT
<213> ORGANISM: Homo sapiens

<400> SEQUENCE: 8

Cys Pro Pro Arg Cys Glu Cys Ser Ala Gln Asp Arg Ala Val Leu Cys
1               5                   10                  15

His Arg Lys Arg Phe Val Ala Val Pro Glu Gly Ile Pro Thr Glu Thr
                20                  25                  30
```

-continued

```
Arg Leu Leu Asp Leu Gly Lys Asn Arg Ile Lys Thr Leu Asn Gln Asp
         35                  40                  45

Glu Phe Ala Ser Phe Pro His Leu Glu Glu Leu Glu Leu Asn Glu Asn
         50                  55                  60

Ile Val Ser Ala Val Glu Pro Gly Ala Phe Asn Asn Leu Phe Asn Leu
 65                  70                  75                  80

Arg Thr Leu Gly Leu Arg Ser Asn Arg Leu Lys Leu Ile Pro Leu Gly
                 85                  90                  95

Val Phe Thr Gly Leu Ser Asn Leu Thr Lys Leu Asp Ile Ser Glu Asn
                100                 105                 110

Lys Ile Val Ile Leu Leu Asp Tyr Met Phe Gln Asp Leu Tyr Asn Leu
             115                 120                 125

Lys Ser Leu Glu Val Gly Asp Asn Asp Leu Val Tyr Ile Ser His Arg
         130                 135                 140

Ala Phe Ser Gly Leu Asn Ser Leu Glu Gln Leu Thr Leu Glu Lys Cys
145                 150                 155                 160

Asn Leu Thr Ser Ile Pro Thr Glu Ala Leu Ser His Leu His Gly Leu
                165                 170                 175

Ile Val Leu Arg Leu Arg His Leu Asn Ile Asn Ala Ile Arg Asp Tyr
             180                 185                 190

Ser Phe Lys Arg Leu Tyr Arg Leu Lys Val Leu Glu Ile Ser His Trp
         195                 200                 205

Pro Tyr Leu Asp Thr Met Thr Pro Asn Cys Leu Tyr Gly Leu Asn Leu
     210                 215                 220

Thr Ser Leu Ser Ile Thr His Cys Asn Leu Thr Ala Val Pro Tyr Leu
225                 230                 235                 240

Ala Val Arg His Leu Val Tyr Leu Arg Phe Leu Asn Leu Ser Tyr Asn
                245                 250                 255

Pro Ile Ser Thr Ile Glu Gly Ser Met Leu His Glu Leu Leu Arg Leu
             260                 265                 270

Gln Glu Ile Gln Leu Val Gly Gly Gln Leu Ala Val Val Glu Pro Tyr
         275                 280                 285

Ala Phe Arg Gly Leu Asn Tyr Leu Arg Val Leu Asn Val Ser Gly Asn
     290                 295                 300

Gln Leu Thr Thr Leu Glu Glu Ser Val Phe His Ser Val Gly Asn Leu
305                 310                 315                 320

Glu Thr Leu Ile Leu Asp Ser Asn Pro Leu Ala Cys Asp Cys Arg Leu
                325                 330                 335

Leu Trp Val Phe Arg Arg Arg Trp Arg Leu Asn Phe Asn Arg Gln Gln
             340                 345                 350

Pro Thr Cys Ala Thr Pro Glu Phe Val Gln Gly Lys Glu Phe Lys Asp
         355                 360                 365

Phe Pro Asp Val Leu Leu Pro Asn Tyr Phe Thr Cys Arg Arg Ala Arg
     370                 375                 380

Ile Arg Asp Arg Lys Ala Gln Gln Val Phe Val Asp Glu Gly His Thr
385                 390                 395                 400

Val Gln Phe Val Cys Arg Ala Asp Gly Asp Pro Pro Pro Ala Ile Leu
                405                 410                 415

Trp Leu Ser Pro Arg Lys His Leu Val Ser Ala Lys Ser Asn Gly Arg
             420                 425                 430

Leu Thr Val Phe Pro Asp Gly Thr Leu Glu Val Arg Tyr Ala Gln Val
         435                 440                 445
```

```
-continued

Gln Asp Asn Gly Thr Tyr Leu Cys Ile Ala Ala Asn Ala Gly Gly Asn
    450                 455                 460

Asp Ser Met Pro Ala His Leu His Val Arg
465                 470

<210> SEQ ID NO 9
<211> LENGTH: 24
<212> TYPE: PRT
<213> ORGANISM: Artificial Sequence
<220> FEATURE:
<223> OTHER INFORMATION: Exemplary motif
<220> FEATURE:
<221> NAME/KEY: VARIANT
<222> LOCATION: 1, 3, 4, 6, 8, 9, 11, 13, 14, 16, 17, 18, 19,21, 22, 24
<223> OTHER INFORMATION: Xaa = any amino acid
<220> FEATURE:
<221> NAME/KEY: VARIANT
<222> LOCATION: 2, 5, 7, 12, 15, 23
<223> OTHER INFORMATION: Xaa =  Leu, but also Ile, Val, Met, Phe or Thr
<220> FEATURE:
<221> NAME/KEY: VARIANT
<222> LOCATION: 10
<223> OTHER INFORMATION: Xaa = Asn, but also Cys, Asp, Leu or Trp
<220> FEATURE:
<221> NAME/KEY: VARIANT
<222> LOCATION: 20
<223> OTHER INFORMATION: Xaa = Phe or Leu

<400> SEQUENCE: 9

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa
            20
```

METHOD FOR IDENTIFYING OR DESIGNING A CANDIDATE AGENT THAT INTERACTS WITH LINGO-1 POLYPEPTIDE USING A LINGO-1 THREE-DIMENSIONAL STRUCTURE

RELATED APPLICATIONS

This application claims the benefit of U.S. Provisional Application No. 60/765,443, filed Feb. 3, 2006, which is incorporated herein by reference in its entirety.

TECHNICAL FIELD

This disclosure relates to LINGO-1 polypeptides, LINGO-1 polypeptide/ligand complexes, crystals of LINGO-1 polypeptides, crystals of LINGO-1 polypeptide/ligand complexes, and related methods and software systems.

BACKGROUND

LINGO-1 (LRR and Ig domain-containing, Nogo Receptor-interacting protein) is a transmembrane coreceptor with p75. The coreceptors, with the ligand binding Nogo-66 receptor (NogoR), make up the Nogo receptor complex, which is commonly located on neurons. Disabling the Nogo receptor complex in which LINGO-1 is located can induce myelin and nerve fiber growth. LINGO-1 has been shown to be active in myelin-making cells known as oligodendrocytes, and inhibition of LINGO-1 has also been shown to induce myelin formation. Thus LINGO-1 signaling is predicted to be a negative regulator of myelin production.

SUMMARY

In one aspect, the invention features a crystallized LINGO-1 polypeptide.

In another aspect, the invention features a crystallized polypeptide-ligand complex that includes a LINGO-1 polypeptide and a ligand that is an agonist or an antagonist of the LINGO-1 polypeptide.

In yet another aspect, the invention features a method that includes using a three-dimensional model of a LINGO-1 polypeptide to design an agent that binds the LINGO-1 polypeptide.

In a further aspect, the invention features a method that includes using a three-dimensional model of a LINGO-1 polypeptide-ligand complex to design an agent that binds the LINGO-1 polypeptide.

In another aspect, the invention features a method that includes using a three-dimensional model of a complex including a LINGO-1 polypeptide to design an agent that binds the LINGO-1 polypeptide.

In another aspect, the invention features a method that includes selecting an agent by, e.g., performing rational drug design with a three-dimensional structure of a LINGO-1 polypeptide, or a LINGO-1 polypeptide-ligand complex; contacting the agent with the LINGO-1 polypeptide; and detecting an ability of the agent to bind the LINGO-1 polypeptide. In embodiments, the method further includes one or more of: obtaining a supplemental crystalline complex that includes the LINGO-1 polypeptide and the agent; determining the three-dimensional structure of the supplemental crystalline complex; selecting a second agent by, e.g., performing rational drug design with the three-dimensional structure of the supplemental crystalline complex; contacting the second agent with the LINGO-1 polypeptide; and/or detecting the ability of the second agent to bind the LINGO-1 polypeptide. The method can further include one or more of: synthesizing the second agent; detecting an ability of the second agent to inhibit LINGO-1 activity; and/or detecting an ability of the second agent to increase myelin levels in vitro or in vivo.

In embodiments, the LINGO-1 polypeptide in the compositions and methods disclosed herein includes (or consists essentially of) a leucine-rich repeat (LRR) domain, an immunoglobulin-like (Ig-like) domain, and/or a stalk domain, or a combination thereof. In other embodiments, the LINGO-1 polypeptide includes (or consists essentially of) the amino acid sequence from a mammalian (e.g., human) or nonmammalian origin; for example, the LINGO-1 polypeptide can include (or consist of) the amino acid sequence of SEQ ID NO: 1, or a variant thereof (e.g., a conservative substitution thereof). In other embodiments, the LINGO-1 polypeptide is crystallized, e.g., is capable of diffracting X-rays to a resolution of at least about 3.7 Å. In embodiments, the crystallized LINGO-1 polypeptide has a space group a $P2_12_12$ or $I222$. In other embodiments, the crystallized LINGO-1 polypeptide has unit cell dimensions chosen from one or more of: a=201.5 Å, b=149.7 Å, c=157.5 Å, and $\alpha=\beta=\gamma=90°$, a=148.7 Å, b=158.6 Å, c=200.0 Å, and $\alpha=\beta=\gamma e=90°$, and a=149.6 Å, b=157.3 Å, c=200.3 Å, and/or $\alpha=\beta=\gamma=90°$. In yet another embodiment, the crystallized LINGO-1 polypeptide has a three-dimensional structure that includes the structural coordinates according to Table 2, +/− a root mean square deviation for alpha carbon atoms of not more than 1.5 Å. In another embodiment, the crystallized LINGO-1 polypeptide has a three-dimensional structure that includes the structural coordinates of an atom chosen from one or more atoms of amino acids Asp13, Arg20, Arg22, Arg43, Glu60, Glu62, Leu94, Leu120, Met123, His176, Tyr142, His145, His185, His209, His233, Ala238, Trp346, Arg347, Asn349, Asn351, Arg352, Gln353, Phe396, Arg408, Leu420, Leu426, Phe438, Asp440, Arg446, Tyr447 and/or Ile459 of the LINGO-1 polypeptide as set forth in SEQ ID NO:1.

In other embodiments, the agent designed or screened using the methods disclosed herein inhibits LINGO-1 activity. For example, the agent can bind LINGO-1 at a ligand binding site and/or interfere with an interaction between LINGO-1 and a ligand. In embodiments, the ligand binding site is located on a concave surface of an LRR domain, e.g., a surface of the LRR domain that includes one or more of Trp346 and Arg352; His185, His209 and His233; Asp13; Glu60 and Glu62; or Arg20, Arg22 and Arg43, according to SEQ ID NO:1. In other embodiments, the ligand binding site is located on a convex surface of an LRR domain, e.g., a surface of the LRR domain that includes one or more of Tyr142 and His145; Leu94, Leu120, and Met123; His176; or Ala238, according to SEQ ID NO:1. In other embodiments, the ligand binding site is located on an Ig domain, e.g., a domain that includes one or more of Arg446 and Tyr447; Arg408, Phe438 and Asp440; Phe396; or Leu420, Leu426 and Ile459, according to SEQ ID NO:1.

In embodiments, the methods disclosed herein include providing a composition including a LINGO-1 polypeptide, or a LINGO-1 polypeptide-ligand complex, and/or crystallizing the composition to form a crystalline complex that includes the LINGO-1 polypeptide, or the LINGO-1 polypeptide-ligand complex. The crystalline complex can diffract X-rays to a resolution of at least about 3.7 Å. The methods disclosed herein can additionally include one or more of the following steps: calculating a distance between an atom of the LINGO-1 polypeptide and an atom of the agent; determining the interaction of the agent with the LINGO-1 polypeptide;

comparing the interaction of the agent with the LINGO-1 polypeptide to an interaction of a second agent with the LINGO-1 polypeptide; selecting the agent via computer modeling; synthesizing the agent; detecting the ability of the agent to inhibit LINGO-1 activity; and/or detecting the ability of the agent to increase myelin formation in vitro or in vivo.

In another aspect, the invention features an agent designed or selected using the methods disclosed herein.

In another aspect, the invention features a software system that includes instructions for causing a computer system to accept information relating to the structure of a LINGO-1 polypeptide, accept information relating to a candidate agent, and determine binding characteristics of the candidate agent to the LINGO-1 polypeptide. The determination of binding characteristics can be based on the information relating to the structure of the LINGO-1 polypeptide, and the information relating to the candidate agent.

In yet another aspect, the invention features a computer program residing on a computer readable medium having a plurality of instructions stored thereon, which, when executed by one or more processors, cause the one or more processors to accept information relating to the structure of a complex comprising a LINGO-1 polypeptide, accept information relating to a candidate agent, and determine binding characteristics of the candidate agent to the LINGO-1 polypeptide. The determination of binding characteristics can be based on the information relating to the structure of the LINGO-1 polypeptide and the information relating to the candidate agent.

In another aspect, the invention features a method that includes accepting information relating to the structure of a LINGO-1 polypeptide and modeling the binding characteristics of the LINGO-1 polypeptide with a candidate agent. The method can be implemented by a software system.

In yet another aspect, the invention features a computer program residing on a computer readable medium having a plurality of instructions stored thereon, which, when executed by one or more processors, cause the one or more processors to accept information relating to a structure of a LINGO-1 polypeptide and model the binding characteristics of the LINGO-1 polypeptide with a candidate agent.

In another aspect, the invention features a software system that includes instructions for causing a computer system to accept information relating to a structure of a LINGO-1 polypeptide and model the binding characteristics of the LINGO-1 polypeptide with a candidate agent.

In a further aspect, the invention features a method of modulating LINGO-1 activity in a subject that includes: selecting, e.g., using the methods described herein (e.g., by rational drug design), an agent that is capable of modulating LINGO-1 activity and administering an effective amount of the agent to the subject, such that the LINGO-1 activity is modulated.

In another aspect, the invention features a method of treating a subject having a condition associated with LINGO-1 activity that includes: selecting, e.g., using the methods described herein (e.g., by rational drug design), an agent that is capable of affecting LINGO-1 activity and administering a therapeutically effective amount of the agent to a subject in need thereof.

In yet another aspect, the invention features a method of prophylactically treating a subject susceptible to a condition associated with LINGO-1 activity that includes determining that the subject is susceptible to the condition associated with LINGO-1 activity, selecting, e.g., using the methods described herein (e.g., by rational drug design), an agent that is capable of effecting LINGO-1 activity, and administering a therapeutically effective amount of the agent to the subject.

In embodiments, the agent used in the methods disclosed herein, e.g., the therapeutic and prophylactic methods disclosed herein, inhibits LINGO-1 activity and/or increases myelin levels in vivo. In embodiments, the condition is a demyelinating disease, e.g., multiple sclerosis.

Other features and advantages of the invention will be apparent from the description, drawings and claims.

DESCRIPTION OF DRAWINGS

FIG. 1 is the amino acid sequence of a histidine-tagged LINGO-1 polypeptide (amino acids 1-516 plus 6-His-tag) (SEQ ID NO:1). The fragment used for crystallization is underlined.

FIG. 5A is a top view of the tetrameric structure; FIG. 5B is a view of the interacting surfaces between the two monomers; and FIG. 5C is a side view of the tetrameric structure.

FIGS. 7A-1 to 7A-3 show the sequence of a pSMEG plasmid (SEQ ID NO:2).

FIGS. 8A-8B depict the full length amino acid and nucleotide sequence of human LINGO-1 (SEQ ID NO:3 and 4, respectively). The coding sequence is encoded by nucleotides 53 to 1915 of SEQ ID NO:4.

DETAILED DESCRIPTION

In general, this disclosure relates to LINGO-1 polypeptides, LINGO-1 polypeptide/ligand complexes, crystals of LINGO-1 polypeptides, crystals of LINGO-1 polypeptide/ligand complexes, and related methods and software systems. Without wishing to be bound by theory, it is believed that crystal structures of LINGO-1 polypeptides and crystals of LINGO-1 polypeptide/ligand complexes can be useful for designing or identifying ligands that can interact with LINGO-1 polypeptides.

Ligands that interact with LINGO-1 polypeptides can inhibit or increase LINGO-1 activity. As an example, LINGO-1 inhibition has been shown to induce myelin formation. Therefore, it is believed that identification of LINGO-1 inhibitors may be useful for treatment of disorders characterized by myelin deficiencies, such as multiple sclerosis, Pelizaeus-Merzbacher's disease, central nervous system trauma, leukodystrophies such as Krabbe disease or Canavan Disease, or vitamin B12 deficiencies.

Figure 2:
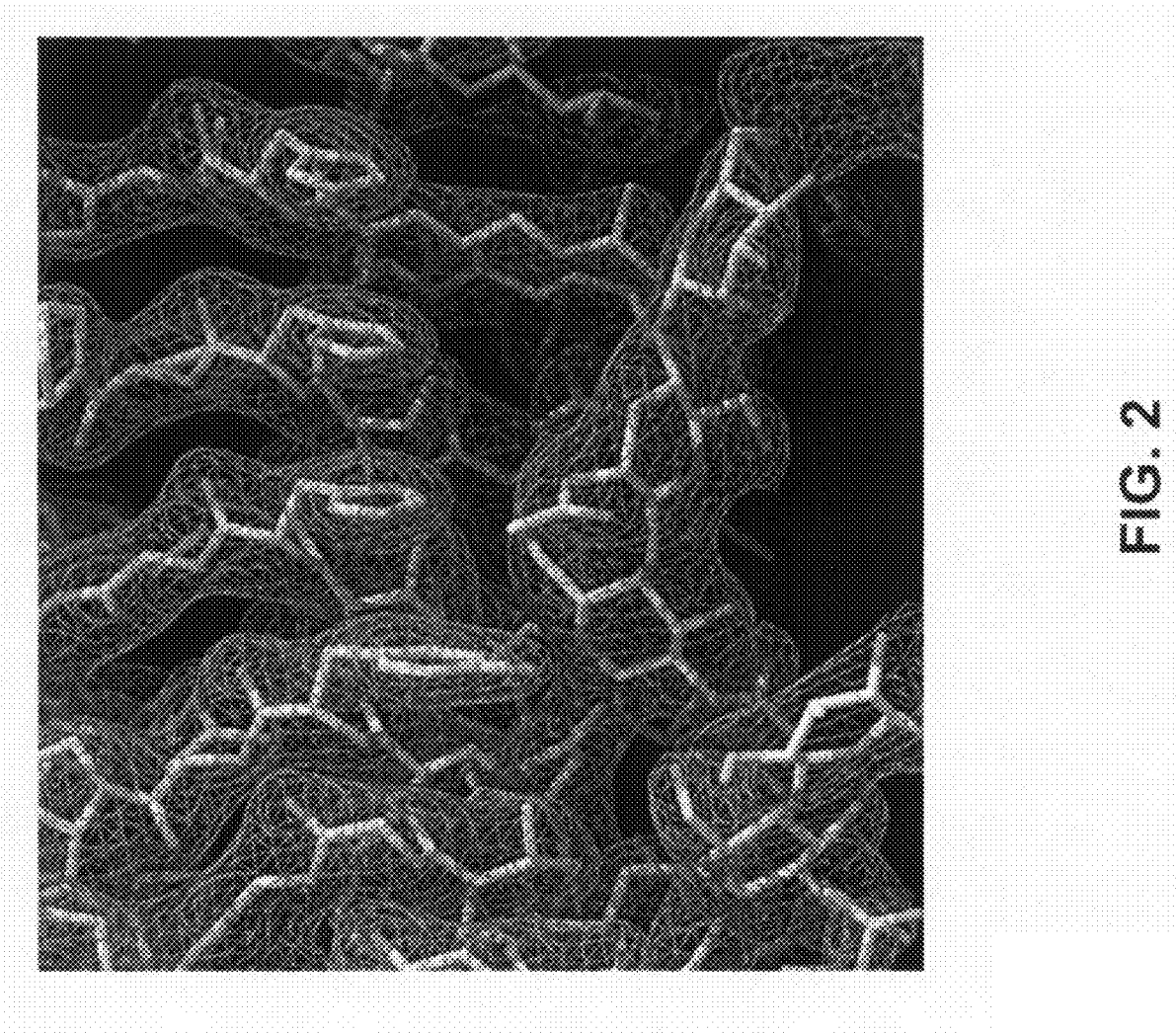
FIG. 2 is a 2fo-fc electron density map for the refined 2.7 Å resolution LINGO-1 structure (see also Table 1).
Figure 3:
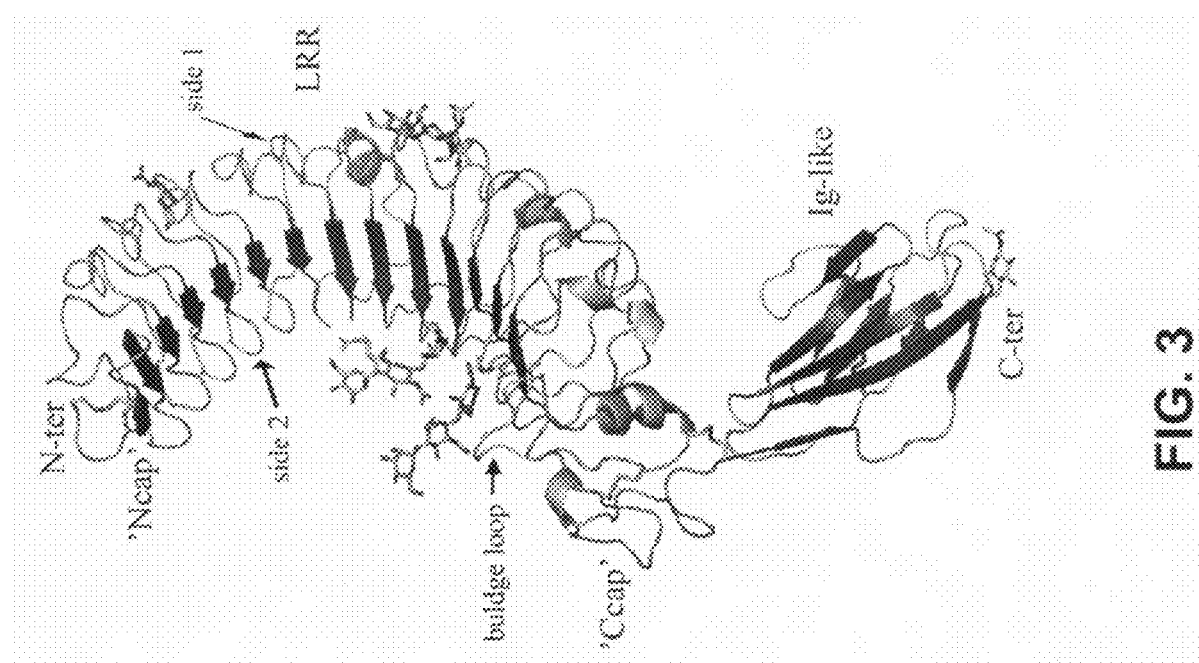
FIG. 3 is a ribbon diagram of a LINGO-1 monomer.

FIG. 1 is the amino acid sequence (SEQ ID NO:1) of a fragment of human LINGO-1 polypeptide (LINGO-1K549$_{his6}$) that includes a leucine-rich repeat (LRR) domain (amino acids 1-382), an immunoglobulin-like (Ig-like) domain (residues 383-477), a stalk region (amino acids 478-516), and a hexahistidine tag fused to the C-terminus of the stalk region. The hexahistidine tag facilitated purification. Not present in the LINGO-1K549$_{his6}$ polypeptide is a 33 amino acid signal sequence that is found at the N-terminus of the full-length human LINGO-1. The wildtype sequence also includes a transmembrane domain and a short cytoplasmic tail at the C-terminus of the protein (Mi et al., *Nat. Neurosci.* 7:221-228, 2004). FIG. 2 is an electron density map for a LINGO-1K549$_{his6}$ structure solved to 2.7 Å resolution (see Table 1). FIG. 3 is a ribbon diagram illustrating the structure of the LINGO-1K549$_{his6}$ polypeptide. The coordinates of a crystal structure of the LINGO-1K549$_{his6}$ polypeptide are provided in Table 2.

To determine the structure of LINGO-1, a human LINGO-1-polypeptide can be prepared and crystallized as described below. In general, the human LINGO-1 polypeptide can be prepared as desired. For example, in some embodiments, the human LINGO-1 polypeptide is expressed from a DNA plasmid. The expression can be driven by a promoter, such as an inducible promoter or a constitutive promoter, such as a cytomegalovirus promoter. The human LINGO-1 polypeptide can be expressed as a fusion protein with a suitable tag, such as a polyhistidine (e.g., hexahistidine), glutathione-S-transferase (GST), myc, HA, Strep, or FLAG tag. The tag can facilitate isolation of the human LINGO-1 polypeptide from cells, such as from bacterial cells or from a mammalian cell line. For example, the human LINGO-1 polypeptide can be expressed in and isolated from Chinese Hamster Ovary (CHO) cells. For example, the human LINGO-1 polypeptide can be fused to a hexahistidine tag and isolated by contacting a cell extract with a Nickel resin (e.g., a Nickel-nitrilotriacetic acid (Ni-NTA) resin) to bind the hexahistidine tag, and then releasing the polypeptide by washing the resin with a buffer containing imidazole. Further, a fusion LINGO-1 polypeptide can be cleaved at a protease site engineered into the fusion protein, such as at or near the site of fusion between the polypeptide and the tag.

The human LINGO-1 polypeptide can be placed in solution for collecting spectral data, NMR data, or for growing a crystal. For example, the human LINGO-1 polypeptide can be crystallized in the presence of a salt (e.g., a sodium salt and/or ammonium salt). Crystals can be grown by various methods, such as, for example, sitting or hanging drop vapor diffusion. In general, crystallization can be performed at a temperature of from about 4° C. to about 60° C. (e.g., from about 10° C. to about 45° C., such as at about 12° C., about 15° C., about 18° C., about 20° C., about 25° C., about 30° C., about 32° C., about 35° C., about 37° C.).

In general, a crystal of the human LINGO-1 polypeptide can diffract X-rays to a resolution of about 3.7 Å or less (e.g., about 3.6 Å or less, about 3.5 Å or less, about 3.2 Å or less, about 3.0 Å or less, about 2.7 Å or less, about 2.4 Å or less, about 2.3 Å or less, about 2.2 Å or less, about 2.1 Å or less, about 2.0 Å or less, about 1.9 Å or less, about 1.8 Å or less, about 1.7 Å or less, about 1.6 Å or less, about 1.5 Å or less, or about 1.4 Å or less). In some embodiments, a crystal of the human LINGO-1 polypeptide can diffract X-rays to a resolution of from about 1.7 Å to about 3.7 Å (e.g., the crystal of the human LINGO-1 polypeptide can diffract X-rays to about 2.7 Å, about 3.5 Å or about 3.6 Å).

In certain embodiments, a crystal of the human LINGO-1 polypeptide belongs to space group I222 with unit cell parameters a=148.7 Å, b=158.6 Å, c=200.0 Å, and $\alpha=\beta=\gamma=90°$. In other embodiments, a crystal of the human LINGO-1 polypeptide belongs to space group I222 with unit cell parameters a=149.6 Å, b=157.3 Å, c=200.3 Å, and $\alpha=\beta=\gamma=90'$. In other embodiments, a crystal of the human LINGO-1 polypeptide belongs to space group P2$_1$2$_1$2 with unit cell parameters a=201.5 Å, b=149.7 Å, c=157.5 Å, and $\alpha=\beta=\gamma=90°$. The space group refers to the overall symmetry of the crystal, and includes point symmetry and space symmetry. In certain embodiments, a crystal of the human LINGO-1 polypeptide belongs to space group I222 and contains two molecules of the human LINGO-1 polypeptide in the asymmetric unit. In other embodiments, a crystal of the human LINGO-1 polypeptide belongs to space group P2$_1$2$_1$2 and contains four molecules of the human LINGO-1 polypeptide in the asymmetric unit. The asymmetric unit is the smallest unit from which the crystal structure can be generated by making use of the symmetry operations of the space group. A crystal is generally made up of the motif defined by the space-group symmetry operations on the asymmetric units, and a translation of that motif through the crystal lattice.

Structural data describing a crystal can be obtained, for example, by X-ray diffraction. X-ray diffraction data can be collected by a variety of sources, X-ray wavelengths and detectors. In some embodiments, rotating anodes and synchrotron sources (e.g., Advanced Light Source (ALS), Berkeley, Calif.; or Advanced Photon Source (APS), Argonne, Ill.) can be used as the source(s) of X-rays. In certain embodiments, X-rays for generating diffraction data can have a wavelength of from about 0.5 Å to about 1.6 Å (e.g., about 0.7 Å, about 0.9 Å, about 1.0 Å, about 1.1 Å, about 1.3 Å, about 1.4 Å, about 1.5 Å, or about 1.6 Å). In some embodiments, area detectors and/or charge-couple devices (CCDs) can be used as the detector(s).

X-ray diffraction data of a crystal of the human LINGO-1 polypeptide can be used to obtain the structural coordinates of the atoms in the complex. The structural coordinates are Cartesian coordinates that describe the location of atoms in three-dimensional space in relation to other atoms in the complex. For example, the structural coordinates listed in Table 2 are the structural coordinates of a crystalline human LINGO-1 polypeptide. The structural coordinates of Table 2 describe the location of atoms of the human LINGO-1 polypeptide (SEQ ID NO:5), (SEQ ID NO:6), (SEQ ID NO:7) and (SEQ ID NO:8) in relation to each other. The structural coordinates can be modified by mathematical manipulation, such as by inversion or integer additions or subtractions. As such, structural coordinates are relative coordinates. For example, structural coordinates describing the location of atoms in the human LINGO-1 polypeptide are not specifically limited by the actual x, y, and z coordinates of Table 2.

The structural coordinates of the human LINGO-1 polypeptide can be used to derive a representation (e.g., a two dimensional representation or three dimensional representation) of the polypeptide or a fragment of the polypeptide. Such representations can be useful for a number of applications, including, for example, the visualization, identification and characterization of an active site of the polypeptide. In certain embodiments, a three-dimensional representation can include the structural coordinates of the human LINGO-1 polypeptide according to Table 2, ± a root mean square (rms) deviation from the alpha carbon atoms of amino acids of not more than about 1.5 Å (e.g., not more than about 1.0 Å, not more than about 0.5 Å).

RMS deviation is the square root of the arithmetic mean of the squares of the deviations from the mean, and is a way of expressing deviation or variation from structural coordinates. Conservative substitutions (see discussion below) of amino acids can result in a molecular representation having structural coordinates within the stated rms deviation. For example, two molecular models of polypeptides that differ from one another by conservative amino acid substitutions can have coordinates of backbone atoms within a stated rms deviation, such as less than about 1.5 Å (e.g., less than about 1.0 Å, less than about 0.5 Å). Backbone atoms of a polypeptide include the alpha carbon ($C_\alpha$ or CA) atoms, carbonyl carbon (C) atoms, and amide nitrogen (N) atoms.

Various software programs allow for the graphical representation of a set of structural coordinates to obtain a representation of the human LINGO-1 polypeptide or a fragment of the polypeptide. In general, such a representation should accurately reflect (relatively and/or absolutely) structural coordinates, or information derived from structural coordinates, such as distances or angles between features. In some embodiments, the representation is a two-dimensional figure, such as a stereoscopic two-dimensional figure. In certain embodiments, the representation is an interactive two-dimensional display, such as an interactive stereoscopic two-dimensional display. An interactive two-dimensional display can be, for example, a computer display that can be rotated to show different faces of a polypeptide or a fragment of a polypeptide. In some embodiments, the representation is a three-dimensional representation. As an example, a three-dimensional model can be a physical model of a molecular structure (e.g., a ball-and-stick model). As another example, a three dimensional representation can be a graphical representation of a molecular structure (e.g., a drawing or a figure presented on a computer display). A two-dimensional graphical representation (e.g., a drawing) can correspond to a three-dimensional representation when the two-dimensional representation reflects three-dimensional information, for example, through the use of perspective, shading, or the obstruction of features more distant from the viewer by features closer to the viewer. In some embodiments, a representation can be modeled at more than one level. As an example, when the three-dimensional representation includes a polypeptide, such as a human LINGO-1 polypeptide, the polypeptide can be represented at one or more different levels of structure, such as primary (amino acid sequence), secondary (e.g., α-helices and β-sheets), tertiary (overall fold), and quaternary (oligomerization state) structure. A representation can include different levels of detail. For example, the representation can include the relative locations of secondary structural features of a protein without specifying the positions of atoms. A more detailed representation could, for example, include the positions of atoms.

In some embodiments, a representation can include information in addition to the structural coordinates of the atoms in the human LINGO-1 polypeptide. For example, a representation can provide information regarding the shape of a solvent accessible surface, the van der Waals radii of the atoms of the model, and the van der Waals radius of a solvent (e.g., water). Other features that can be derived from a representation include, for example, electrostatic potential, the location of voids or pockets within a macromolecular structure, and the location of hydrogen bonds and salt bridges.

An agent that interacts with (e.g., binds) the human LINGO-1 polypeptide can be identified or designed by a method that includes using a representation of the polypeptide or a fragment of the polypeptide. Exemplary types of representations include the representations discussed above. In some embodiments, the representation can be of an analog polypeptide or polypeptide fragment. A candidate agent that interacts with the representation can be designed or identified by performing computer fitting analysis of the candidate agent with the representation. In general, an agent is a molecule. Examples of agents include polypeptides, nucleic acids (including DNA or RNA), steroids and non-steroidal organic compounds. An agent that interacts with a polypeptide (e.g., a human LINGO-1 polypeptide) can interact transiently or stably with the polypeptide. The interaction can be mediated by any of the forces noted herein, including, for example, hydrogen bonding, electrostatic forces, hydrophobic interactions, and van der Waals interactions.

As noted above, X-ray crystallography can be used to obtain structural coordinates of the human LINGO-1 polypeptide. However, such structural coordinates can be obtained using other techniques including NMR techniques. Additional structural information can be obtained from spectral techniques (e.g., optical rotary dispersion (ORD), circular dichroism (CD)), homology modeling, and computational methods (e.g., computational methods that can include data from molecular mechanics, computational methods that include data from dynamics assays).

In some embodiments, the X-ray diffraction data can be used to construct an electron density map of the human LINGO-1 polypeptide or a fragment of the polypeptide, and the electron density map can be used to derive a representation (e.g., a two dimensional representation, a three dimensional representation) of the human LINGO-1 polypeptide.

Creation of an electron density map typically involves using information regarding the phase of the X-ray scatter. Phase information can be extracted, for example, either from the diffraction data or from supplementing diffraction experiments to complete the construction of the electron density map. Methods for calculating phase from X-ray diffraction data include, for example, multiwavelength anomalous dispersion (MAD), multiple isomorphous replacement (MIR), multiple isomorphous replacement with anomalous scattering (MIRAS), single isomorphous replacement with anomalous scattering (SIRAS), reciprocal space solvent flattening, molecular replacement, or any combination thereof. These methods generate phase information by making isomorphous structural modifications to the native protein, such as by including a heavy atom or changing the scattering strength of a heavy atom already present, and then measuring the diffraction amplitudes for the native protein and each of the modified cases. If the position of the additional heavy atom or the change in its scattering strength is known, then the phase of each diffracted X-ray can be determined by solving a set of simultaneous phase equations. The location of heavy atom sites can be identified using a computer program, such as SHELXD (Bruker-AXS, Madison, Wis.) or SHELXS (Sheldrick, Institut Anorg. Chemie, Göttingen, Germany), and XPREP (Bruker-AXS, Madison, Wis.); and diffraction data can be processed using computer programs such as MOSFLM, SCALA, SOLOMON, and SHARP ("The CCP4 Suite: Programs for Protein Crystallography," *Acta Crystallogr.* Sect. D, 54:905-921, 1997; deLa Fortelle and Brigogne, *Meth. Enzym.* 276:472-494, 1997). The phase of X-ray scatter for a crystalline human LINGO-1 polypeptide, for example, can be determined by SIRAS using crystals of a platinum derivative of the LINGO-1 polypeptide. To create a platinum derivative of a crystalline LINGO-1 polypeptide, the crystalline LINGO-1 polypeptide can be soaked in a solution containing platinum. Phases obtained by SIRAS from the platinum derivative can then be refined using, for example, non-crystallographic symmetry (NCS) averaging and phase extension in a computer program such as DM (Cowtan and Main, *Acta Cryst.* D49:148-157, 1993). The resulting model can be further derived by molecular replacement with a second data set. For example, a model derived from a crystalline LINGO-1 polypeptide having space group 1222 can be refined using molecule replacement with a data set from a crystalline LINGO-1 polypeptide having space group $P2_12_12$. Phases obtained by SIRAS from crystals of the native crystalline polypeptide and the platinum derivative can then be used to create an electron density map of the LINGO-1 polypeptide.

The electron density map can be used to derive a representation of a polypeptide or a fragment of a polypeptide by aligning a three-dimensional model of a polypeptide with the electron density map. For example, the electron density map corresponding to the native crystalline human LINGO-1 polypeptide can be aligned with the electron density map corresponding to the platinum derivative of the crystalline human LINGO-1 polypeptide complex derived by an isomorphous replacement method.

The alignment process results in a comparative model that shows the degree to which the calculated electron density map varies from the model of the previously known polypeptide or the previously known complex. The comparative model is then refined over one or more cycles (e.g., two cycles, three cycles, four cycles, five cycles, six cycles, seven cycles, eight cycles, nine cycles, ten cycles) to generate a better fit with the electron density map. Software programs such as CNS (Brunger et al, *Acta Crystallogr. D*54:905-921, 1998) and REFMAC (Collaborative Computational Project, Number 4. The CCP4 suite: Programs for Protein Crystallography, *Acta Crystallogr. D*50:760-776, 1994) can be used to refine the model. The quality of fit in the comparative model can be measured by, for example, an $R_{factor}$ or $R_{free}$ value. A smaller value of $R_{factor}$ or $R_{free}$ generally indicates a better fit. Misalignments in the comparative model can be adjusted to provide a modified comparative model and a lower $R_{factor}$ or $R_{free}$ value. The adjustments can be based on information relating to variations of the human LINGO-1 polypeptide (e.g., sequence variation information, alternative structure information, heavy atom derivative information) as appropriate. As an example, in embodiments in which a model of a heavy atom derivative of a crystalline LINGO-1 polypeptide is used, an adjustment can include fitting an approximate model of the native LINGO-1 polypeptide over the model of the heavy atom derivative. As another example, in certain embodiments, an adjustment can include replacing an amino acid in the previously known LINGO-1 polypeptide with an amino acid having a similar structure (a conservative amino acid change). When adjustments to the modified comparative model satisfy a best fit to the electron density map, the resulting model is that which is determined to describe the polypeptide or complex from which the X-ray data was derived. Methods of such processes are disclosed, for example, in Carter and Sweet, eds., "Macromolecular Crystallography" in *Methods in Enzymology*, Vol. 277, Part B, New York: Academic Press, 1997, and articles therein, e.g., Jones and Kjeldgaard, "Electron-Density Map Interpretation," p. 173, and Kleywegt and Jones, "Model Building and Refinement Practice," p. 208.

A machine, such as a computer, can be programmed in memory with the structural coordinates of the human LINGO-1 polypeptide together with a program capable of generating a graphical representation of the structural coordinates on a display connected to the machine. A software system can also be designed and/or utilized to accept and store the structural coordinates. The software system can be capable of generating a graphical representation of the structural coordinates. The software system can also be capable of accessing external databases to identify one or more candidate agents likely to interact with the human LINGO-1 polypeptide.

A machine having a memory containing structure data or a software system containing such data can aid in the rational design or selection of a human LINGO-1 polypeptide agonist of a human LINGO-1 polypeptide antagonist. For example, such a machine or software system can aid in the evaluation of the ability of an agent to associate with the human LINGO-1 polypeptide, or can aid in the modeling of compounds or proteins related by structural or sequence homology to the human LINGO-1 polypeptide. As used herein, an agonist refers to a compound that enhances at least one activity of the human LINGO-1 polypeptide, and an antagonist refers to a compound that inhibits or counteracts at least one activity of the human LINGO-1 polypeptide. For example, a compound may function as an antagonist of the human LINGO-1 polypeptide by, for example, increasing the rate of myelin production by a neural cell, or by inhibiting interaction of the human LINGO-1 polypeptide with the Nogo receptor complex.

The machine can produce a representation (e.g., a two dimensional representation, a three dimensional representation) of the human LINGO-1 polypeptide or a fragment of the polypeptide. A software system, for example, can cause the machine to produce such information. The machine can include a machine-readable data storage medium including a data storage material encoded with machine-readable data. The machine-readable data can include structural coordinates of atoms of the human LINGO-1 polypeptide. Machine-readable storage media (e.g., data storage material) include, for example, conventional computer hard drives, floppy disks, DAT tape, CD-ROM, DVD, and other magnetic, magneto-optical, optical, and other media which may be adapted for use with a machine (e.g., a computer). The machine can also have a working memory for storing instructions for processing the machine-readable data, as well as a central processing unit (CPU) coupled to the working memory and to the machine-readable data storage medium for the purpose of processing the machine-readable data into the desired three-dimensional representation. A display can be connected to the CPU so that the three-dimensional representation can be visualized by the user. Accordingly, when used with a machine programmed with instructions for using the data (e.g., a computer loaded with one or more programs of the sort described herein) the machine is capable of displaying a graphical representation (e.g., a two dimensional graphical representation, a three-dimensional graphical representation) of any of the polypeptides, polypeptide fragments, complexes, or complex fragments described herein.

A display (e.g., a computer display) can show a representation of the human LINGO-1 polypeptide or a fragment of the human LINGO-1 polypeptide. The user can inspect the representation and, using information gained from the representation, generate a model of the human LINGO-1 polypeptide or polypeptide fragment bound to a ligand. The model can be generated, for example, by altering a previously existing representation of the human LINGO-1 polypeptide. Optionally, the user can superimpose a three-dimensional model of an agent on the representation of the human LINGO-1 polypeptide. The agent can be an agonist (e.g., a candidate agonist) of the human LINGO-1 polypeptide. In some embodiments, the agent can be a known compound or a fragment of a known compound. In certain embodiments, the agent can be a previously unknown compound, or a fragment of a previously unknown compound.

It can be desirable for the agent to have a shape that complements the shape of the active site. There can be a preferred distance, or range of distances, between atoms of the agent and atoms of the human LINGO-1 polypeptide. Distances longer than a preferred distance may be associated with a weak interaction between the agent and active site (e.g., the active site of the human LINGO-1 polypeptide). Distances shorter than a preferred distance may be associated with repulsive forces that can weaken the interaction between the agent and the polypeptide. A steric clash can occur when distances between atoms are too short. A steric clash occurs when the locations of two atoms are unreasonably close together, for example, when two atoms are separated by a distance less than the sum of their van der Waals radii. If a steric clash exists, the user can adjust the position of the agent relative to the human LINGO-1 polypeptide (e.g., a rigid body translation or rotation of the agent) until the steric clash is relieved. The user can adjust the conformation of the agent or of the human LINGO-1 polypeptide in the vicinity of the agent in order to relieve a steric clash. Steric clashes can also be removed by altering the structure of the agent, for example, by changing a "bulky group," such as an aromatic ring, to a smaller group, such as to a methyl or hydroxyl group, or by changing a rigid group to a flexible group that can accommodate a conformation that does not produce a steric clash. Electrostatic forces can also influence an interaction between an agent and a ligand-binding domain. For example, electrostatic properties can be associated with repulsive forces that can weaken the interaction between the agent and the human LINGO-1 polypeptide. Electrostatic repulsion can be relieved by altering the charge of the agent, e.g., by replacing a positively charged group with a neutral group.

Forces that influence binding strength between a candidate agent and the human LINGO-1 polypeptide, respectively, can be evaluated in the polypeptide/agent model. These can include, for example, hydrogen bonding, electrostatic forces, hydrophobic interactions, van der Waals interactions, dipole-dipole interactions, π-stacking forces, and cation-π interactions. The user can evaluate these forces visually, for example by noting a hydrogen bond donor/acceptor pair arranged with a distance and angle suitable for a hydrogen bond. Based on the evaluation, the user can alter the model to find a more favorable interaction between the human LINGO-1 polypeptide and the agent. Altering the model can include changing the three-dimensional structure of the polypeptide without altering its chemical structure, for example by altering the conformation of amino acid side chains or backbone dihedral angles. Altering the model can include altering the position or conformation of the agent, as described above. Altering the model can also include altering the chemical structure of the agent, for example by substituting, adding, or removing groups. For example, if a hydrogen bond donor on the human LINGO-1 polypeptide is located near a hydrogen bond donor on the agent, the user can replace the hydrogen bond donor on the agent with a hydrogen bond acceptor.

The relative locations of an agent and the human LINGO-1 polypeptide, or their conformations, can be adjusted to find an optimized binding geometry for a particular agent to the human LINGO-1 polypeptide. An optimized binding geometry is characterized by, for example, favorable hydrogen bond distances and angles, maximal electrostatic attractions, minimal electrostatic repulsions, the sequestration of hydrophobic moieties away from an aqueous environment, and the absence of steric clashes. The optimized geometry can have the lowest calculated energy of a family of possible geometries for the human LINGO-1 polypeptide/agent complex. An optimized geometry can be determined, for example, through molecular mechanics or molecular dynamics calculations.

A series of representations of the human LINGO-1 polypeptide having different bound agents can be generated. A score can be calculated for each representation. The score can describe, for example, an expected strength of interaction between the human LINGO-1 polypeptide and the agent. The score can reflect one of the factors described above that influence binding strength. The score can be an aggregate score that reflects more than one of the factors. The different agents can be ranked according to their scores.

Steps in the design of the agent can be carried out in an automated fashion by a machine. For example, a representation of the human LINGO-1 polypeptide can be programmed in the machine, along with representations of candidate agents. The machine can find an optimized binding geometry for each of the candidate agents to an active site, and calculate a score to determine which of the agents in the series is likely to interact most strongly with the human LINGO-1 polypeptide.

A software system can be designed and/or implemented to facilitate these steps. Software systems (e.g., computer programs) used to generate representations or perform the fitting analyses include, for example: MCSS, Ludi, QUANTA® (macromolecular X-ray crystallography software), Insight II® (biological compound modeling and simulation software), Cerius$^2$® (modeling and simulation software), CHARMm® (software for simulation of biological macromolecules) CHARMm® (software for simulation of biological macromolecules), and Modeler from Accelrys, Inc. (San Diego, Calif.); SYBYL® (molecular modeling software), Unity, FleXX, and LEAPFROG from TRIPOS, Inc. (St. Louis, Mo.); AUTODOCK (Scripps Research Institute, La Jolla, Calif.); GRID (Oxford University, Oxford, UK); DOCK (University of California, San Francisco, Calif.); and Flo+ and Flo99 (Thistlesoft, Morris Township, N.J.). Other useful programs include ROCS, ZAP, FRED, Vida, and Szybki from Openeye Scientific Software (Santa Fe, N. Mex.); Maestro, Macromodel, and Glide from Schrodinger, LLC (Portland, Oreg.); MOE (Chemical Computing Group, Montreal, Quebec), Allegrow (Boston De Novo, Boston, Mass.), CNS (Brunger, et al., *Acta Crystall. Sect. D* 54:905-921, 1997) and GOLD (Jones et al., *J. Mol. Biol.* 245:43-53, 1995). The structural coordinates can also be used to visualize the three-dimensional structure of the human LINGO-1 polypeptide using MOLSCRIPT, RASTER3D, or PYMOL (Kraulis, *J. Appl. Crystallogr.* 24: 946-950, 1991; Bacon and Anderson, *J. Mol. Graph.* 6: 219-220, 1998; DeLano, The PYMOL Molecular Graphics System (2002) DeLano Scientific, San Carlos, Calif.).

The agent can, for example, be selected by screening an appropriate database, can be designed de novo by analyzing the steric configurations and charge potentials of a human LINGO-1 polypeptide in conjunction with the appropriate software systems, and/or can be designed using characteristics of known ligands, such as the neurotrophin receptor p75 and the Nogo receptor (NogoR). The method can be used to design or select agonists or antagonists of the human LINGO-1 polypeptide. A software system can be designed and/or implemented to facilitate database searching, and/or agent selection and design.

Once an agent has been designed or identified, it can be obtained or synthesized and further evaluated for its effect on the activity of the human LINGO-1 polypeptide. For example, the agent can be evaluated by contacting it with the human LINGO-1 polypeptide and measuring the effect of the agent on polypeptide activity. A method for evaluating the agent can include an activity assay performed in vitro or in vivo.

An activity assay can be a cell-based assay, for example. A cell based assay can include monitoring the effect of a candidate agent on myelin production. Such assays for human LINGO-1 polypeptide inhibitors may involve contacting a candidate inhibitor with cells expressing the human LINGO-1 polypeptide and assaying for an effect on cell morphology. For example, a neural cell line can be contacted with a candidate agent and the cells monitored for an effect on oligodendrocyte differentiation. Decreases in LINGO-1 activity have been shown to increase the differentiation of cells into mature oligodendrocytes, as evidenced by increases in the length of cell processes (Mi et al., *Nat. Neuroscience*

8:745-751, 2005). LINGO-1 activity can also be assayed by measuring levels of proteins involved in myelin production, such as myelin-associated glycoprotein (MAG), a protein expressed at the onset of myelination; myelin basic protein (MBP), the major protein component of myelin; and other myelin components including oligodendrocyte-myelin glycoprotein (OMpg), myelin oligodendrocyte glycoprotein (MOG) and cyclic nucleotide phosphodiesterase (CNPase). LINGO-1 inhibitors have been shown to promote the upregulation of expression of each of these proteins (Mi et al., *Nat. Neuroscience* 8:745-751, 2005). Protein levels can be assayed by standard protein detection techniques, such as immunohistochemistry by Western blot analysis or in situ hybridization in cultured cells or whole tissue sections.

Depending upon the action of the agent on the human LINGO-1 polypeptide, the agent can act either as an agonist or antagonist of human LINGO-1 polypeptide activity. An agonist, for example, may decrease the rate of myelin production, or increase the binding affinity of the human LINGO-1 polypeptide to the Nogo receptor complex. Conversely, an antagonist may increase the rate of myelin production or decrease the binding affinity of the human LINGO-1 polypeptide to the Nogo receptor complex. The agent can be contacted with the human LINGO-1 polypeptide in the presence of one or more components of the Nogo receptor complex (e.g., p75 or Nogo-66) in order to determine whether or not the agent inhibits binding of the human LINGO-1 polypeptide to the Nogo receptor complex. A crystal containing the human LINGO-1 polypeptide bound to the identified agent can be grown and the structure determined by X-ray crystallography. A second agent can be designed or identified based on the interaction of the first agent with the human LINGO-1 polypeptide.

Various molecular analysis and rational drug design techniques are further disclosed in, for example, U.S. Pat. Nos. 5,834,228, 5,939,528 and 5,856,116, as well as in PCT Application No. PCT/US98/16879, published as WO 99/09148.

While certain embodiments have been described, other embodiments are also contemplated.

As an example, while embodiments involving the human LINGO-1 polypeptide have been described, the description herein is more generally directed to any LINGO-1 polypeptide.

A LINGO-1 polypeptide can be a full-length, mature polypeptide, including the full-length amino acid sequence of any isoform of a LINGO-1 polypeptide. An isoform is any of several multiple forms of a protein that differ in their primary structure. The full length amino acid and nucleotide sequences of human LINGO-1 are disclosed in FIGS. 8A-8B.

A LINGO-1 polypeptide can be a fragment of a human LINGO-1 polypeptide, such as a signal sequence, an LRR-type domain, an Ig-like domain, a transmembrane domain, a cytoplasmic domain, or a combination thereof. A fragment of a LINGO-1 polypeptide can include more than 40%, 50%, 60%, 80%, 90% or more of a LINGO-1 polypeptide sequence (e.g., SEQ ID NO:1). For example, a LINGO-1 polypeptide can include one or more of the following domains: an LRR-type domain (e.g., about amino acids 1-382 of SEQ ID NO:1), or a fragment or selected residue thereof (e.g., one or more of amino acids Asp13, Arg20, Arg22, Arg43, Glu60, Glu62, Leu94, Leu120, Met123, His176, Tyr142, His145, His185, His209, His 233, Ala238, Trp346, Arg347, Asn349, Asn351, Arg352, and/or Gln353, of SEQ ID NO:1); an Ig-like domain (e.g., about amino acids 383-477 of SEQ ID NO:1), or a fragment or selected residue thereof (e.g., one or more of amino acids Phe396, Arg408, Leu420, Leu426, Phe438, Asp440, Arg446, Tyr447 and/or Ile459 of SEQ ID NO:1); and/or a stalk region (e.g., about amino acids 478-516 of SEQ ID NO:1), or a fragment or selected residue thereof. In other embodiments, the LINGO-1 polypeptide can contain one or more of the active sites and/or structural folds, as described herein. The LINGO-1 polypeptide may contain one or more conservative amino acid substitutions that yield a similar three-dimensional structure, as described herein. For example, in some embodiments, the LINGO-1 polypeptide (or fragment thereof) includes up to 5, 10, 20, 30, 50, 75, 100, 150, or 200 or more conservative substitutions from a predetermined sequence, e.g., a human LINGO-1 amino acid sequence (e.g., SEQ ID NO:1).

A LINGO-1 polypeptide can have an active site. For example, the LRR-like domain includes a likely active site of a LINGO-1 polypeptide. In general, an active site can include a site of ligand binding, or a site of phosphorylation, glycosylation, alkylation, acylation, or other covalent modification. A site of ligand binding can be a site of a site of binding of a component of the Nogo receptor complex, or an agonist or antagonist of LINGO-1 activity. An active site can include a glycosylation site. A ligand binding site can include accessory binding sites adjacent to or proximal to the actual site of binding that may affect activity upon interaction with the ligand. Candidate active sites of the human LINGO-1 polypeptide can be identified by comparing the structure of the LINGO-1 polypeptide with homologous structures of other known polypeptides. For example, one or more active sites of the human LINGO-1 polypeptide can be identified by comparing the structure of the LINGO-1 polypeptide with the structure of the platelet membrane glycoprotein Gp1bα. A candidate active site on LINGO-1 including Trp346 and Arg352 was identified by its similarity to the structure of a ligand-binding site on Gp1bα. Cavities located on the surface of the human LINGO-1 polypeptide also represent candidate ligand-binding sites.

An active site of the human LINGO-1 polypeptide can include amino acids of SEQ ID NO:1 (FIG. 1). For example, an active site of the human LINGO-1 polypeptide can include one or more of amino acids Asp13, Arg20, Arg22, Arg43, Glu60, Glu62, Leu94, Leu120, Met123, His176, Tyr142, His145, His185, His209, His233, Ala238, Trp346, Arg347, Asn349, Asn351, Arg352, Gln353, Phe396, Arg408, Leu420, Leu426, Phe438, Asp440, Arg446, Tyr447 and Ile459 as set forth in the amino acid positions of SEQ ID NO:1. An active site can include a subset of amino acids located at a particular region of the human LINGO-1 polypeptide. For example, an active site can be located on the concave surface of the LRR-domain and include Trp346 and Arg352; His 185, His209, and His233; Asp13; Glu60 and Glu62; or Arg20, Arg22, and Arg43 of SEQ ID NO:1. In another example, an active site can be located on the convex surface of the LRR-domain and include Tyr142 and His145; Leu94, Leu120, and Met123; His176; or Ala238 of SEQ ID NO:1. In another example, an active site can be located on the Ig-domain and include Arg446 and Tyr447; Arg408, Phe438, and Asp440; Phe396; or Leu420, Leu426, and Ile459 of SEQ ID NO:1.

The numbering of the amino acids of the human LINGO-1 polypeptide may be different than that set forth herein, and the sequence of the human LINGO-1 polypeptide may contain certain conservative amino acid substitutions that yield the same or similar three-dimensional structure. For example, the numbering of the human LINGO-1 polypeptide may be different than that set forth in FIG. 1, and the sequence of the human LINGO-1 polypeptide may contain conservative amino acid substitutions but yield the same structure as that defined by the coordinates of Table 2 and illustrated in FIGS. 2-4 and FIGS. 5A-5C. Corresponding amino acids and conservative substitutions in other isoforms or analogs are easily identified by visual inspection of the relevant amino acid sequences or by using commercially available homology software programs (e.g., MODELLAR, MSI Management Simulations, Inc., San Diego, Calif.). The crystal structure coordinates shown in Table 2 were determined from a crystal having space group $P2_12_12$, but the same coordinates +/− a root mean square deviation for alpha carbon atoms of not more than 1.5 Å, can correspond to a crystalline LINGO-1 polypeptide having a different space group, such as I222.

An analog is a polypeptide having conservative amino acid substitutions. A conservative substitution can include switching one amino acid for another with similar polarity, steric arrangement, or of the same class (e.g., hydrophobic, acidic or basic), and includes substitutions having an inconsequential effect on the three-dimensional structure of the human LINGO-1 polypeptide with respect to identification and design of agents that interact with the polypeptide, as well as for molecular replacement analyses and/or for homology modeling.

Variants or mutants of a LINGO-1 polypeptide can be used in the methods, compositions, and three-dimensional models disclosed herein. A variant or mutant of a LINGO-1 polypeptide, or fragment thereof, includes chimeric proteins, labeled proteins (e.g., radiolabeled proteins), fusion proteins, mutant proteins, proteins having similar (e.g., substantially similar) sequences (e.g., proteins having amino acid substitutions (e.g., conserved amino acid substitutions), deletions, insertions), protein fragments, mimetics, so long as the variant has at least a portion of an amino acid sequence of a native protein, or at least a portion of an amino acid sequence of substantial sequence identity to the native protein. In embodiments, the mutant LINGO-1 differs from the amino acid sequence of SEQ ID NO:1 or a fragment thereof by up to 5, 10, 20, 30, 50, 75, 100, 150, or 200 or more amino acid residues. In other embodiments, the mutant LINGO-1 is at least about 70%, 80%, 90%, 95% or more identical to a LINGO-1 polypeptide sequence, e.g., a human LINGO-1 polypeptide (e.g., SEQ ID NO:1).

A "chimeric protein" or "fusion protein" is a fusion of a first amino acid sequence encoding a polypeptide with a second amino acid sequence, wherein the first and second amino acid sequences do not occur naturally as part of a single polypeptide chain.

As used herein, the term "substantially similar" (or "substantially" or "sufficiently" "homologous" or "identical") is used herein to refer to a first amino acid or nucleotide sequence that contains a sufficient number of identical or equivalent (e.g., with a similar side chain, e.g., conserved amino acid substitutions) amino acid residues or nucleotides to a second amino acid or nucleotide sequence such that the first and second amino acid or nucleotide sequences have similar activities. Sequences similar or homologous (e.g., at least about 85% sequence identity) to the sequences disclosed herein are also part of this application. In some embodiments, the sequence identity can be about 90%, 91%, 92%, 93%, 94%, 95%, 96%, 97%, 98%, 99% or higher.

Calculations of "homology" or "sequence identity" between two sequences are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). Typically, the length of a reference sequence aligned for comparison purposes is at least 30%, preferably at least 40%, more preferably at least 50%, even more preferably at lo least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In one embodiment, the percent identity between two amino acid sequences is determined using the Needleman and Wunsch ((1970) *J. Mol. Biol.* 48:444-453) algorithm which has been incorporated into the commercially available GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another embodiment, the percent identity between two nucleotide sequences is determined using the commercially available GAP program in the GCG software package, using a NWSgapdna.CMP matrix and a gap weight of 40, 50, 60, 30 70, or 80 and a length weight of 1, 2, 3, 4, 5, or 6. Parameters typically used to determine percent homology are a Blossum 62 scoring matrix with a gap penalty of 12, a gap extend penalty of 4, and a frameshift gap penalty of 5. The percent identity between two amino acid or nucleotide sequences can also be determined using the s algorithm of E. Meyers and W. Miller ((1989) *CABIOS* 4:11-17) which has been incorporated into the ALIGN program (version 2.0), using a PAM120 weight residue table, a gap length penalty of 12 and a gap penalty of 4.

A LINGO-1 polypeptide can originate from a nonmammalian or mammalian species. A mammalian LINGO-1 polypeptide can originate from a human, for example. Exemplary nonhuman mammals include a nonhuman primate (such as a monkey or ape), a mouse, rat, goat, cow, bull, pig, horse, sheep, wild boar, sea otter, cat, and dog. Exemplary nonmammalian species include chicken, turkey, shrimp, alligator, and fish. The LINGO-1 amino acid and nucleotide sequences from several mammalian and nonmammalian species (including, for example, human, mouse, rat, dog, chimpanzee and chicken) are known in the art (see e.g., Mi et al. (2005) *Nat. Neuroscience* 8:745-751; Carim-Todd, L. et al. (2003) *Eur. J. Neurosci.* 18(12):3167-3182; and Okafuji et al. (2005) *Gene Expr. Patterns* 6(1): 57-62).

An agent can be, for example, a chemical compound (e.g., a polypeptide, nucleic acid, peptidomimetic). A peptidomimetic is a chemical compound that can mimic the ability of a peptide to recognize certain physiological molecules, such as proteins and nucleic acids. In some instances, the peptidomimetic includes non-peptidic structural elements that are capable of mimicking or antagonizing the biological action(s) of a natural parent peptide. For example, scissile peptide bonds can be replaced with one or more non-scissile dipeptide isosteres.

The following example is illustrative and not intended as limiting.

Example

LINGO-1 was crystallized and its structure determined. The human LINGO-1 is a 614 amino acid protein containing a signal sequence, a leucine-rich repeat-like domain, an immunoglobulin-like domain, a stalk domain, a transmembrane domain and a short cytoplasmic tail (Mi et al., *Nat. Neurosci.* 7:221-228, 2004). The extracellular region of human LINGO-1 (including the LRR motifs, the Ig-like domain and the stalk region, and not including the signal sequence) was fused at its C-terminus to a hexahistidine tag (FIG. 1). The resulting LINGO-1K549$_{his6}$ construct was subcloned into a pSMEG vector (SEQ ID NO:2) (FIGS. 6, and 7A-1 to 7A-3) behind a murine cytomegalovirus (CMV) promoter (K549 refers to the lysine that occurs at amino acid position 249 of the full-length human LINGO-1 construct, including the 33 amino acid signal sequence. The signal sequence was not present in the LINGO-1K549$_{his6}$ polypeptide.). The construct was verified by sequencing. Mammalian Chinese hamster ovary (CHO) cells were grown and maintained in a humidified incubator with 5% $CO_2$ at 37° C. Cell culture and DNA transfection for Lec3.2.8.1 cells are described in Zhong et al. (*Biochim. Biophys. Acta* 1723:143-150, 2005). A stable clone for LINGO-1K549$_{his6}$ construct in Lec3.2.8.1 (1042-5) was established by screening with anti-his4 antibody. Procedures for large-scale production of conditioned media for LINGO-1K549$_{his6}$ were as described previously (Zhong et al., *Biochim. Biophys. Acta* 1723:143-150, 2005).

To purify LINGO-1K549$_{his6}$, conditioned CHO media expressing the fusion protein (FIG. 1) was exchanged for a buffer of 50 mM Tris at pH 8.0, 100 mM NaCl, to which a cocktail of protease inhibitors was added (complete inhibitors from Roche, Nutley, N.J.). To capture the fusion protein, Ni-NTA resin was equilibrated in 50 mM Tris, pH 8.0, 100 mM NaCl and then added to the cultured media for batch binding (end-over-end) for 2 hours. Once the cultured media was removed, the Ni-NTA resin was packed into a column. The column was connected to an AKTA Explorer (HPLC) and was washed with 4-5 column volumes of 50 mM Tris, pH 8.0; 100 mM NaCl. The protein was eluted with a 12-column volume gradient from 0% to 100% 50 mM Tris, pH 8.0; 100 mM NaCl, 300 mM imidazole. The collected protein fractions were dialyzed into 50 mM Tris, pH 8.0; 500 mM NaCl. For crystallization, the protein was incubated with Carboxypeptidase A (Sigma, St. Louis, Mo.) for 14-16 hours at 25° C., and then dialyzed into 50 mM MES, pH 6.1; 50 mM NaCl. After dialysis, the protein was loaded onto an SP sepharose column (GE Healthcare) and washed with 4-5 column volumes of 50 mM MES, pH 6.1; 50 mM NaCl. The protein was eluted with a 12-column volume gradient from 0% to 100% 50 mM MES, pH 6.1; 750 mM NaCl. The protein peak fractions were collected, concentrated to 5-8 mg/ml and then loaded onto the gel filtration Superdex 200 column equilibrated with TBS. The protein peak fractions were pooled together and concentrated to 4-5 mg/ml for crystallization. The purified protein was fully glycosylated.

LINGO-1K549$_{his6}$ crystals were obtained using the hanging drop vapor diffusion method at 18° C. Diffraction quality crystals were grown from protein solutions with 4 mg/mL of protein and precipitating solutions of 1.2-1.4 M $(NH_4)_2SO_4$, 0.1 M Na-Citrate, pH 5.0. The protein crystallized in two forms under identical conditions, with both forms found in the same crystallization droplets: I222, with two molecules per asymmetric unit and 74% solvent content, and $P2_12_12$, with four molecules per asymmetric unit and 73% solvent content. For data collection, crystals were gradually transferred from the mother liquor to the stabilizing-cryoprotecting solution containing 2.9 M sodium malonate, pH 5.2 (Holyoak et al., *Biological Crystallography* D59:2356-2358, 2003). This solution, in which crystals were found to be stable over the period of several days and over the pH range 5-7, was used for crystal derivatization. A single derivative that allowed structure determination by the method of single isomorphous replacement with anomalous scattering (SIRAS) was obtained from a platinum derivative, created by soaking the crystals in 50 mM $K_2PtCl_6$ and 2.9 M sodium malonate at pH 7.0 for 24 hours. Prior to data collection, all crystals were flush cooled under a nitrogen stream at 100 K.

Two data sets obtained from crystals of space group I222 were used for phase determination: the 3.5 Å native data set and the 3.6 Å data set for the platinum derivative, both measured in-house with a Saturn92 CCD mounted on an FR-E Cu Kα rotating anode source (Rigaku, Japan). The higher resolution native data set was collected to 2.7 Å at Advanced Photon Source (APS) (Argonne, Ill.) with beamline 22-ID of SER-CAT from a crystal that belongs to the $P2_12_12$ space group. All data were integrated and scaled with HKL2000 (Otwinowski and Minor, *Methods Enzymol.* 276:307-326, 1997).

The initial positions of the platinum (Pt) atoms in the derivative crystal were located with SHELXD (2001, Bruker-AXS, XM, Ver. 6.12; Bruker-AXS, Madison, Wis.) using anomalous differences of Pt atoms at the Cu Kα-edge. The input SAS coefficients were prepared with XPREP (2001 Bruker-AXS, Ver. 6.12; Bruker-AXS, Madison, Wis.). Refinement of heavy-atom parameters, phase calculation and density modification by SOLOMON (Abrahams and Leslie, *Acta Cryst.* D52: 30-42, 1996) were performed with SHARP (de La Fortelle and Bricogne, *Methods Enzymol.* 276:472-494, 1997) at 20-3.6 Å resolution, using both anomalous and isomorphous differences from the native and derivative data sets. The final 3.6 Å single isomorphous replacement with anomalous scattering (SIRAS) maps produced with SHARP were of interpretable quality and revealed two LINGO-1 molecules in the asymmetric unit. SHARP phases were further improved by two-fold non-crystallographic symmetry (NCS) averaging and phase extension to 3.5 Å in DM (Cowtan and Main, *Acta Cryst.* D49:148-157, 1993). The resulting maps allowed us to build an initial, 90% complete (~855 residues) model with QUANTA (Accelrys, Inc., San Diego, Calif.). This model was then used for molecular replacement with the $P2_12_12$ data set to utilize the higher 2.7 Å resolution data. A clear solution for four molecules in the asymmetric unit was identified with PHASER (McCoy et al., *Acta Cryst.* D61:458-464, 2005). The I222 and $P2_12_12$ crystal forms share the same tetrameric packing, in which the tetramer can be built by replicating a dimer around the two-fold axis. Subsequent rounds of rebuilding and refinement against the 2.7 Å data set were done with the (Crystallographic Object)-Oriented Toolkit (COOT) (Emsley and Cowtan, *Acta Crys. D* 60:2126-2132, 2004) and REFMAC (Murshudov et al., *Acta Crystallogr. D* 53:240-255, 1997).

The final model contains four protein molecules (residues A1-477, B3-475, C2-477, and D3-476), 39 N-acetylglucosamine and 12 mannose residues, and 310 water molecules. Residues 1-2 at the N-termini of B, C and D; 476-477 at the C-termini of B and D; and residues D32-34 were not modeled into the structure due to the lack of adequate electron density, presumably because of disordering. Geometric analysis of the final refined structure performed with MolProbity places 94% of all residues in favored regions and 0.16% as outliers. Statistics for data collection, phasing and refinement are summarized in Table 1.

Table 2 lists the crystal structure coordinates as deduced from the crystal of space group $P2_12_12$ (see Table 1). The native and derivative structures having space group I222 revealed essentially the same structure and were used to help with phasing. In Table 2, the "#" column assigns an index to each atom for which coordinates are given. The "name" column indicates what type of atom, and the "res" column indicates what type of residue the atom belongs to. The "chain" indicates which polypeptide the atom belongs to. "Res #" gives the residue number for the atom. For example, atom number 1 (the first row in Table 2) is the Nitrogen (N) of Thr1 (according to the sequence set forth in SEQ ID NO:1). Its x, y, and z structural coordinates are given in the X, Y, and Z columns, respectively. The column headed "occ" describes the occupancy assigned to the atom (1.00=full occupancy), and the "B" column provides B factors (or temperature factors) in units of $Å^2$. The column labeled "element" lists the atom's element symbol. Water is denoted by "HOH." "NAG" and "MAN" indicate N-acetylglucosamine and mannose residues, respectively.

TABLE 1

Statistics for data collection, phasing and refinement

| Data collection | Native 1 | $K_2PtCl_6$ | Native 2 |
|---|---|---|---|
| Space Group | I222 | I222 | $P2_12_12$ |
| Unit Cell Dimensions | | | |
| a (Å) | 148.7 | 149.6 | 201.5 |
| b (Å) | 158.6 | 157.3 | 149.7 |
| c (Å) | 200.0 | 200.3 | 157.5 |
| $α = β = γ$ (deg) | 90 | 90 | 90 |
| Source | FR-E CuKα | FR-E CuKα | APS ID-22 |
| Max. resolution (Å) | 3.5 | 3.6 | 2.7 |
| Reflections (total/unique) | 251,385/29,544 | 201,963/27,406 | 915,151/129,631 |
| Completeness (%) | 97.1 (98.8) | 99.1 (99.8) | 98.9 (94.7) |
| $R_{sym}^{a}$ (%) | 11.7 (50.2) | 10.5 (45.9) | 9.0 (61.2) |
| I/σ(I) | 16.1 (3.6) | 15.3 (3.4) | 20.6 (1.2) |

| Phasing | SIRAS | |
|---|---|---|
| Anom. I/σ(I) (4.5 Å/3.6 Å) | 2.3/1.2 | |
| $R_{iso}^{b}$ (%) | 43.6 | |
| $R_{ano}^{b}$ (%) | 8.6 | |
| Number of Pt sites | 15 | |
| Phasing Power$^c$ (4.5 Å/3.6 Å) | anomalous 1.13/0.6 | isomorphous 1.1/0.73 |
| Mean Figure of Merit$^d$ (4.5 Å/3.6 Å) | 0.45/0.25 | |

| Model refinement | Native 2 | |
|---|---|---|
| Resolution (Å) | 50.0-2.7 | |
| Number of Reflections | 122,982 | |
| Completeness (%) | 98.7 (91.3) | |
| $R_{factor}/R_{free}$* (%) | 21.5/25.5 | |
| No. of protein atoms | 15,114 | |
| No. of carbohydrate atoms | 700 | |
| No. of waters | 310 | |
| r.m.s. deviations from ideal geometry | bonds (Å) 0.009 | angles (deg) 1.25 |

$^aR_{sym} = Σ Σ_i |I(h)_i − <I(h)>|/Σ Σ_i I(h)_i$, where $<I(h)>$ is the mean intensity. Numbers in parentheses reflect statistics for the highest resolution shells.
$^bR_{iso} = Σ|F_{nat}(h) − F_{Pt}(h)|/Σ F_{nat}(h)$ and $R_{ano}$ is calculated for the amplitudes of the positive and negative counterparts of the Bijvoet pairs.
$^c$Phasing Power is defined by $<|F_H|>/<(lack-of-closure)>$, where 'H' represents heavy-atom.
$^d$Mean figure of merit is the estimated mean cosine of the phase error.
*$R_{free}$ is calculated with 5% of the data.

Both crystal forms of LINGO-1 (I222 and $P2_12_12$) revealed a tetrameric structure, consistent with gel filtration data and dynamic light scattering measurements, showing that LINGO-1 exists as a tetramer in solution with a molecular weight of ~240 kDa. FIG. 2 shows a fragment of the electron density for the refined 2.7 Å resolution structure.

An overall view of the monomeric LINGO-1 structure is shown in FIG. 3. Each monomer is formed from two distinct domains: residues 1-382 constitute the N-terminal LRR-domain and residues 383-477 form the C-terminal Ig-like domain. The relative orientation of the two constituent domains gives the monomeric structure a question mark shape.

The LRR-domain (residues 1-382) adopts an elongated arc shape with a parallel 15-stranded β-sheet on the concave inner face and with highly irregular secondary structures on the convex outer face (FIG. 3). In total, there are twelve LRRs, 23 to 25 residues each, that together create a continuous right-handed super-helical assembly. Each LRR begins with a β-strand and has the consensus 24-residue sequence repeat motif: $xL^2xxL^5xL^7xxN^{10}xL^{12}xxL^{15}xxxxF^{20}xxL^{23}x$ (SEQ ID NO:9), where x can be any amino acid; L is a hydrophobic residue, preferentially Leu, but also Ile, Val, Met, Phe or Thr; N are less conserved in nature and includes mostly Asn, but also Cys, Asp, Leu or Trp; and F represents the hydrophobic residue Phe or Leu. The consensus residues at the indicated positions make up the interior of the LRR-domain. As in several other LRR proteins, the N- and C-termini of the LRR hydrophobic core are shielded from the solvent by two LRR caps: 'Ncap' and 'Ccap' (FIG. 3). The 'Ncap' has two antiparallel β-strands with two disulfide bridges at the base (Cys3-Cys9 and Cys7-Cys18), an arrangement that is very close in structure to NogoR (He, et al., Neuron 38:177-185, 2003). The 'Ccap' is also supported by two disulfide bridges (Cys334-Cys357 and Cys336-Cys382) and, like NogoR, has a characteristic motif consisting of one α-helix and three short $3_{10}$-helices. Unlike in the NogoR, however, the interior of the 'Ccap' in LINGO-1 is filled almost entirely with a phenylalanine cluster (six aromatic rings from Phe342, Phe350, Phe362, Phe368, Phe371, Phe380 and one aromatic ring from Tyr379). In addition, a short loop segment (residues 349-353) following the α-helix is integrated into the canonical LRR structure in a slightly different way than in NogoR. The result is such that the top of the 5-residue loop bulges away from the β-sheet into the concave space by at least 7.5 Å, therefore showing a more protruding character than the corresponding segment of the same length in NogoR. The position of the bulge loop (FIG. 3), which corresponds to the ligand binding β-switch loop in the platelet membrane glycoprotein Gplbα (Huizing a et al., Science 297:1176-1179, 2002), combined with a character of the surface-exposed and protruding side chains (Trp346, Arg347, and Asn349, Asn351, Gln353, and Arg352 at the tip of the loop), suggests a likely candidate for interaction with a ligand. The electrostatic surface of the molecule (FIG. 4) reveals a pronounced set of electropositive and electronegative patches on all sides of the LRR-domain, except one relatively large hydrophobic patch found on the N-terminal convex side.

Based on the structure of the tetrameric complex, five subsets of amino acids located on the concave surface of the LRR domain were determined to be candidate ligand binding sites: (1) Trp346 and Arg352; (2) His185, His209, and His233; (3) Asp13; (4) Glu60 and Glu62; and (5) Arg20, Arg22, and Arg43. Likewise, four subsets of amino acids located on the convex surface of the LRR domain were determined to be candidate ligand binding sites: (1) Tyr142 and His145; (2) Leu94, Leu120, and Met123; (8) His176; and (9) Ala238.

After completing the LRR-domain, the polypeptide chain enters the compact Ig-like fold (residues 383-477) which represents the classical β-sandwich of two β-sheets cross-linked by one disulfide bond (Cys407-Cys458). Four strands (A, B, D and E) form one β-sheet and five strands (A', C, C', F and G) make up the second β-sheet. There is one 310 α-helical turn that connects the E and F strands. Comparison with other Ig-like structures indicates that the closest structural analog of the LINGO-11 g-like domain is the Ig3-module of the neural cell adhesion molecule, NCAM (Soroka et al., *Structure* 10:1291-1301, 2003), with the calculated identity between the two sequences of ~30%. Not surprisingly, the majority of the amino acid replacements occurs at the Ig-domain surfaces altering the side chain volumes and/or surface polarity, and most of the conserved amino acids map to the core of the structure and have equivalent conformations to satisfy the fold. The surface electrostatic potential is a combination of negative and positive patches on the ABDE-surface. On the contrary, the opposite A'CC'FG-surface is highly enriched in hydrophobic residues (Ala416, Leu418, Leu420, Leu426, Leu457, Ile459, Ala461, Ala463) surrounded by a number of polar and positively charged residues.

Figure 4:
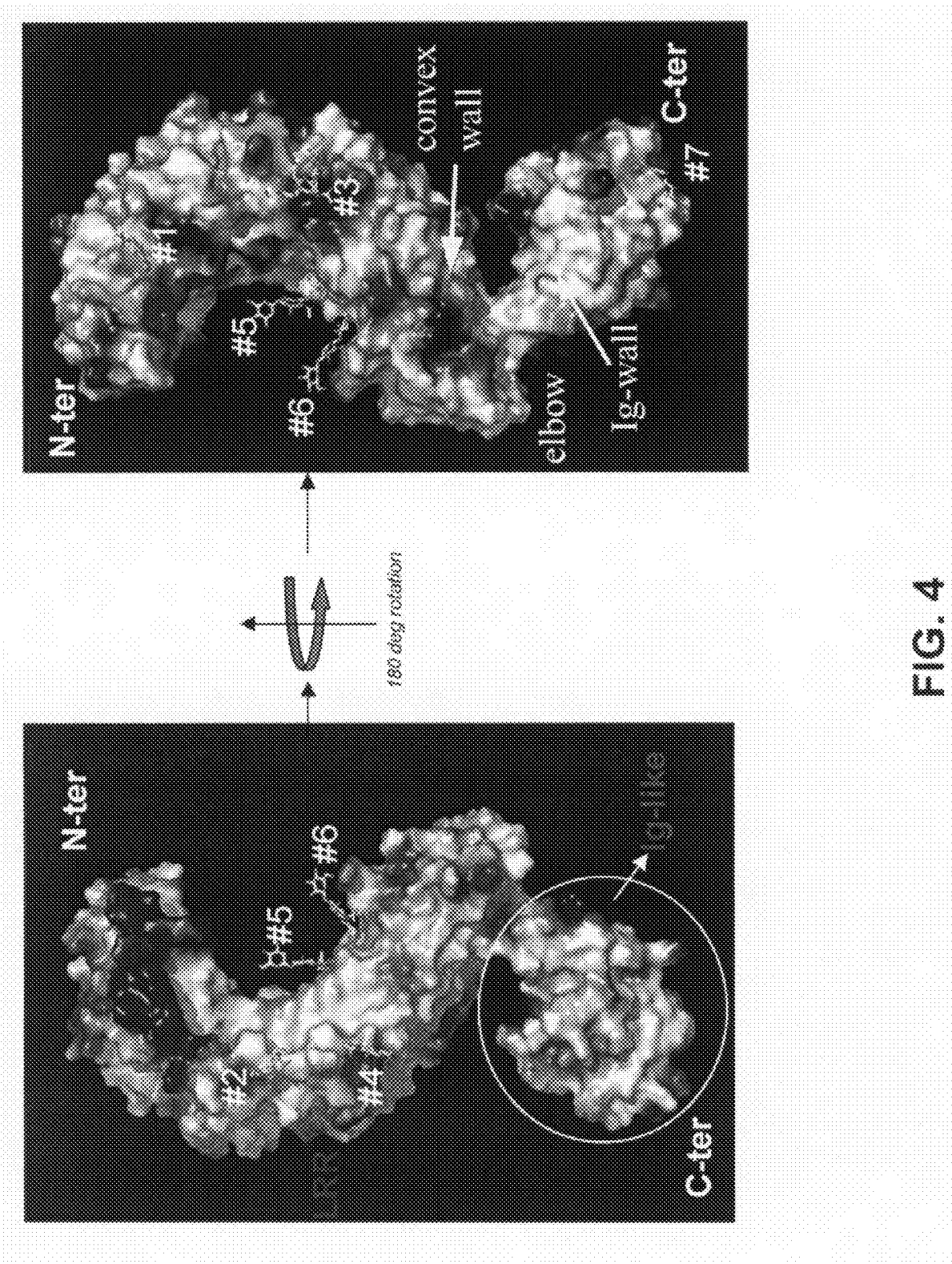
FIG. 4 is a space-filled model of a LINGO-1 monomer. The numbered residues denote glycosylated asparagine residues.

The Ig-domain orientation is such that it projects away from the convex LRR arc creating a wide solvent-exposed cleft at the back of the LRR-domain, with an elbow angle of ~90 degrees (FIG. 4). The walls of the cleft are formed by the C-terminal convex surface of LRR (repeats 10-12 and the Ccap), on one side, and by the A'CC'FG β-sheet of the Ig-domain on the other. The opposing surfaces are relatively far apart and have different properties. The convex surface is made up of mostly polar and charged residues, while the opposing Ig-surface is rather flat and is lined up with the amino acids that are predominantly hydrophobic (as indicated above). Small interdomain interactions occur at the tip of the elbow and involve van der Waals contacts between residues on the FG-loop (Ala463, Gly464) and on the C-terminal portion of LRR (Cys336, Arg337 and Cys382). Of note are the disulfide bond at the tip of the elbow, Cys336-Cys382, and the absence of an interdomain linker (as Arg383 is the first residue of the first β-strand and a component of the ABDE β-sheet). Such linkage between the domains constrains the positioning of the two relative to each other.

Based on the structure of the tetrameric complex, five subsets of amino acids on the Ig domain were determined to be candidate ligand binding sites: (1) Arg446 and Tyr447; (2) Arg408, Phe438, and Asp440; (3) Phe396; and (4) Leu420, Leu426, and Ile459.

Figure 5B:
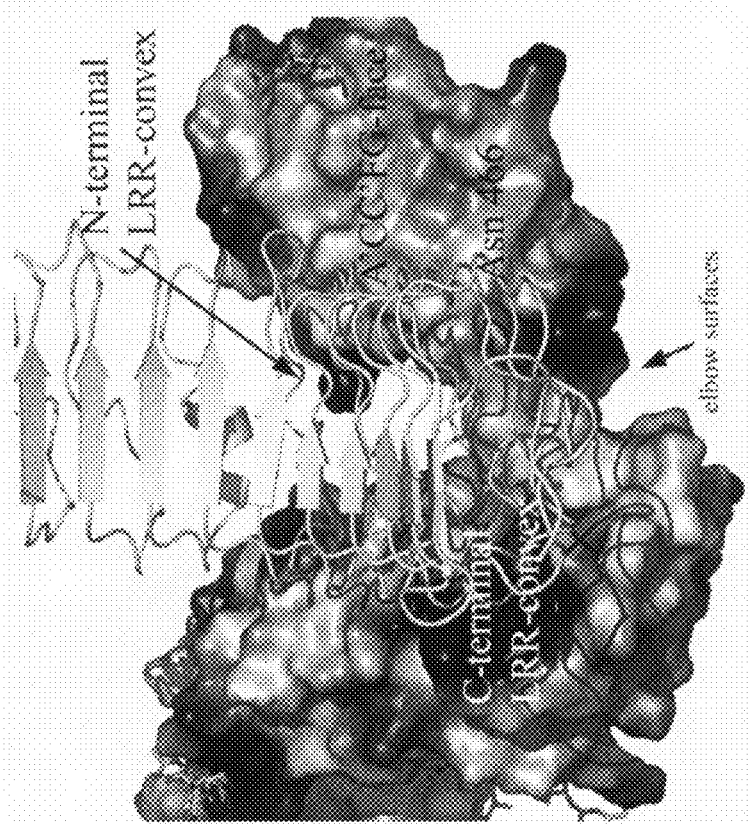
FIGS. 5A-5C are structure diagrams illustrating the tetrameric organization of the LINGO-1 crystal structure.

The glycoform of LINGO-1 in CHO restricted cells is expected to be predominantly high-mannose type glycans such as $Man_5GlcNAc_2$, which is consistent with our mass spectrometry data. The crystallized glycoprotein contains eight typical N-glycosylation consensus sites. Six of them are located in the LRR-domain (Asn105, Asn163, Asn225, Asn235, Asn254, and $Asn3O_2$) and two in the Ig-like domain (Asn466 and Asn453). All of these sites are positioned at the domain surfaces. Electron density can be assigned for carbohydrate moieties at all of these locations, except for the Asn466 site. The latter, although located at the surface, is wrapped up closely with a symmetry-related LINGO-1 partner, as described below and as shown in FIG. 5B. Since the protein packing leaves no room for glycosylation at Asn466, the N-glycan linked to Asn466 would prevent the LINGO-1 tetramerization observed in the crystals. The oligosaccharides at the remaining seven sites are spread over the structure as shown by the numbered residues in FIG. 4, where #1 corresponds to Asn 105, #2 to Asn163, #3 to Asn 225, #4 to Asn 235, #5 to Asn 254, #6 to Asn 302, and #7 to Asn 453. Out of four faces of the LRR-domain, only the convex outer surface is completely bare of carbohydrates, a finding consistent with its role in self-association. The concave and the two side surfaces, each bearing two N-glycan binding sites, are largely covered by carbohydrate. The last carbohydrate moiety maps to the Ig-face A'CC' FG, proximal to the C-terminus and remote from the intermolecular interface (FIG. 4).

In general, the presence of extensive glycosylation on glycoprotein surfaces limits their accessibility for interaction with ligands, and in most cases the surfaces that are not covered by sugars are where the ligands are predicted to bind (Rudd et al., *JMB* 293:351-366, 1999). Therefore, it seems unlikely that the concave LRR surface of LINGO-1, with two sugar moieties right at the arc centre, can play a major role in accommodating such large protein partners as NogoR or p75. This would be contrary to the other LRR-containing receptors that frequently use the concave surfaces for interaction with their ligands (Bell et al., *Trends Immunol.* 24:528, 2003). Since there is no evidence to suggest that the Asn-linked N-glycans are directly associated with ligand binding, it is also possible that the LINGO-1 glycosylation helps prevent non-specific protein-protein interactions or helps maintain the proper scaffold for subsequent ligand binding.

Figure 5A:
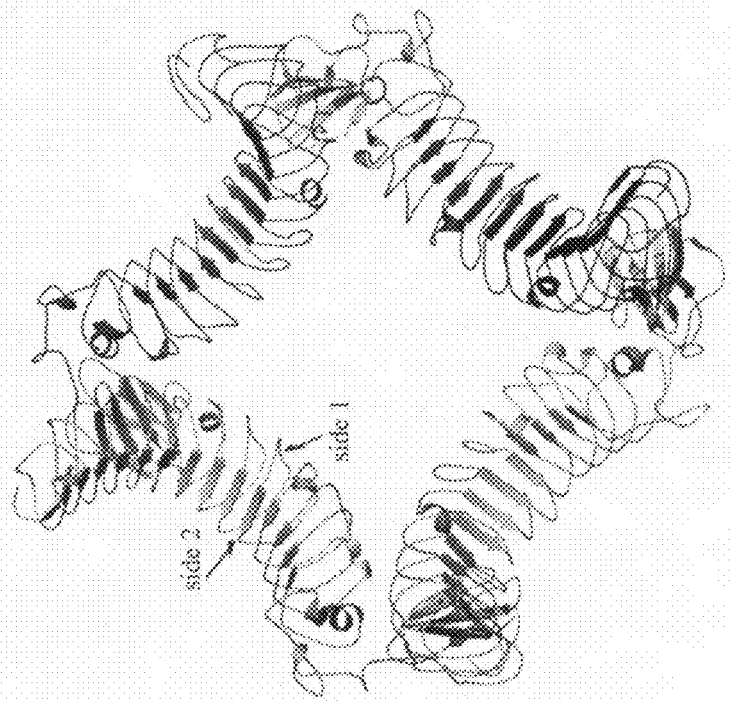
Figure 5C:
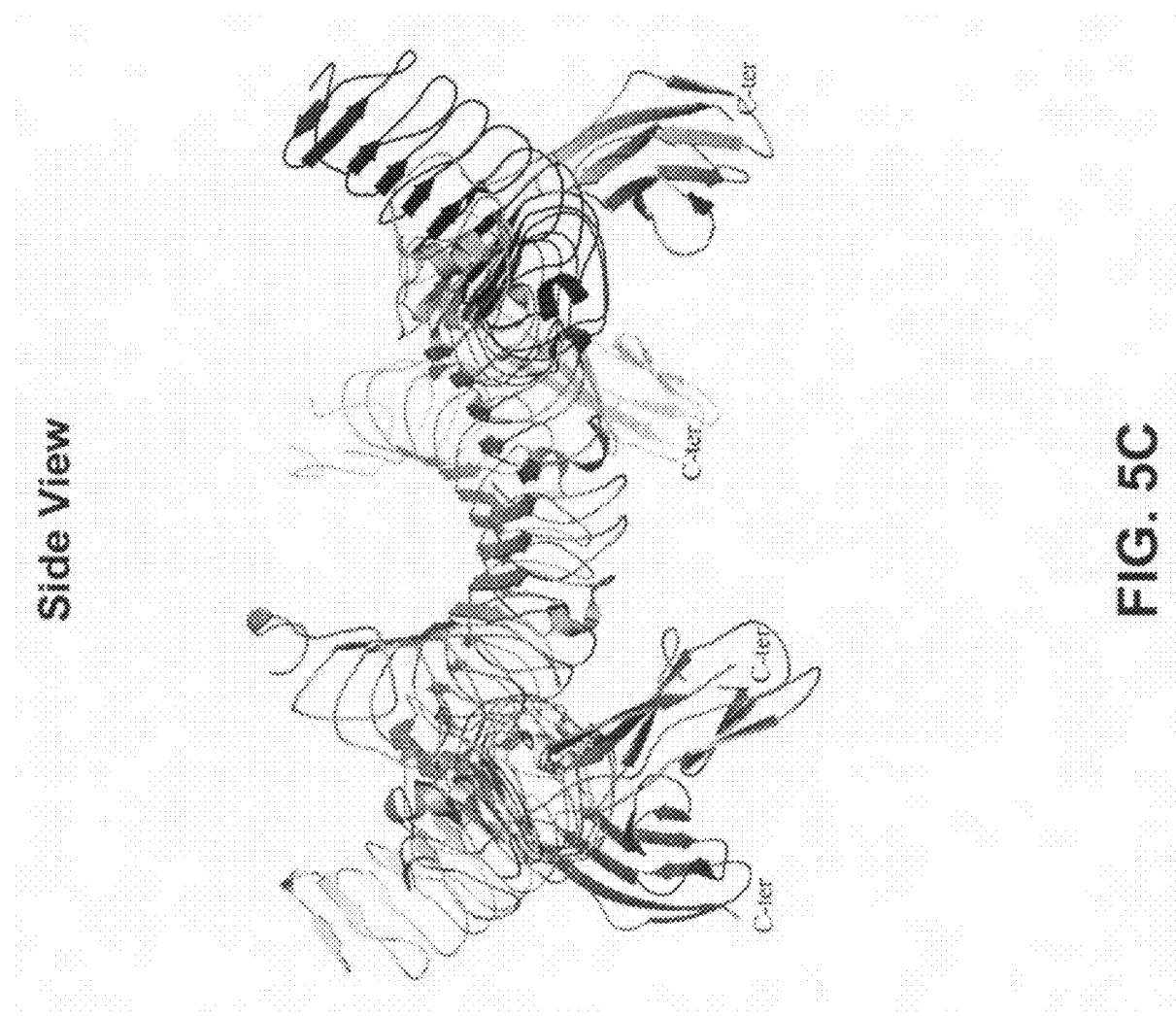
Figure 6:
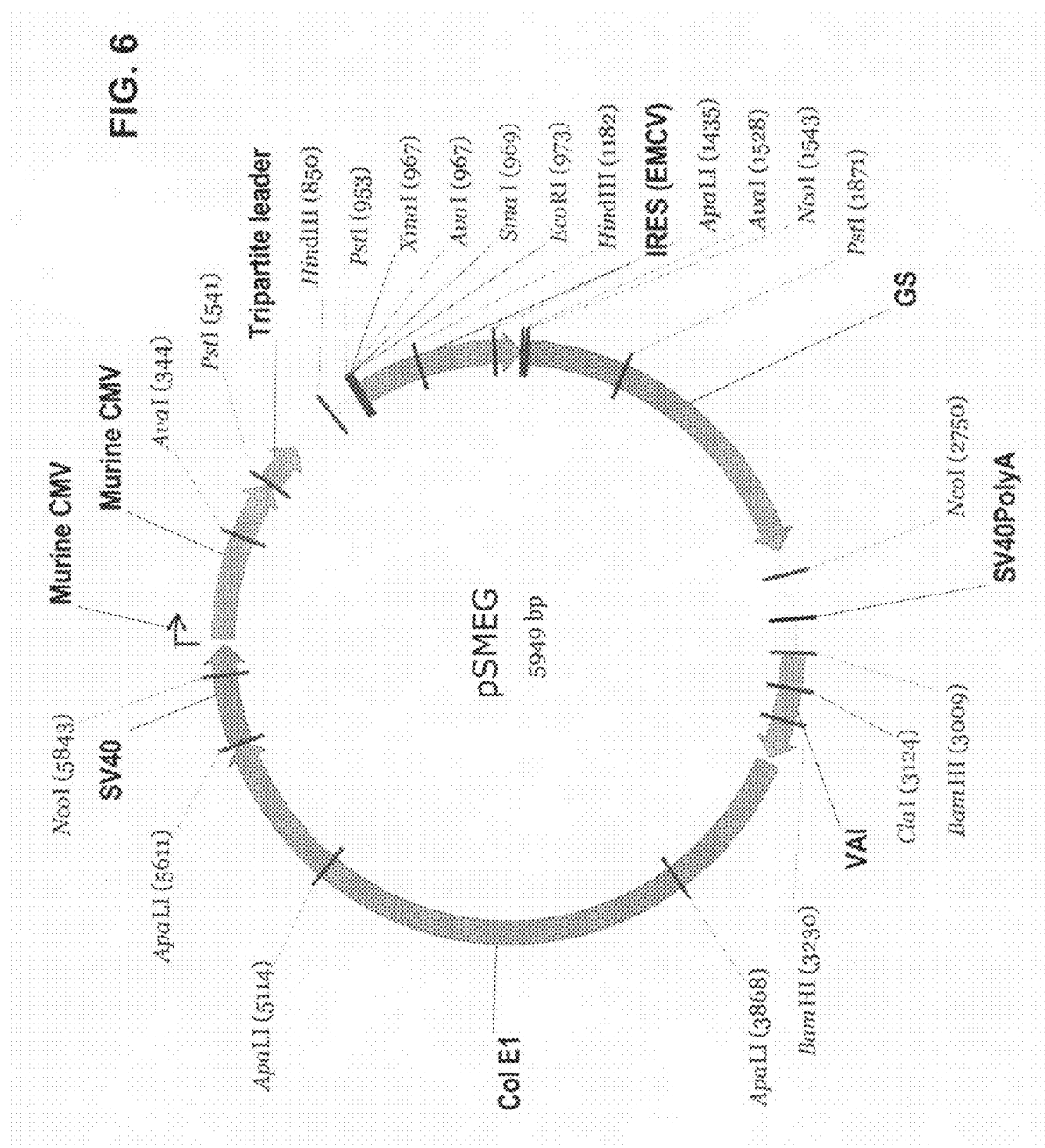
FIG. 6 is a map of a pSMEG plasmid.

Crystallization, size-exclusion chromatography and dynamic light scattering all indicate that LINGO-1 adopts a tetrameric form both in crystals and in solution. In the crystal, the four independent copies of LINGO-1 interact to constitute a condensed tetrameric structure. A pseudo four-fold axis of rotation relates the four molecules in a ring-like structure with a large hole at the center (~40 Å in diameter; outer ring diameter ~95 Å; FIG. 5A). This arrangement places the N-terminal convex side of each LRR-domain at the elbow between the domains of the adjacent molecule (FIG. 5B), reminiscent of a cytokine/receptor binding mode. As in the latter case, the attachment point between two molecules is provided by three surfaces: one formed by the N-terminal curved repeats 1-6 and two elbow surfaces formed, as described above, by the C-terminal curved repeats 11-12, the 'C-cap' and the A'CC'FG β-strands, respectively. Hence, the four LRR-domains interlock the ring in a head-to-tail fashion, and the corresponding Ig-like modules extend from the perimeter of the ring in a landing gear fashion (see FIG. 5C). If we apply this geometry relative to a cell surface, then the protein rotation axis will lie approximately normal to the surface with the membrane-proximal C-terminal ends pointing in the same direction, i.e., towards the cell membrane.

Each intermolecular interface reveals a tight geometric match between the binding surfaces and the precise stereochemical complementarity of the interaction. The solvent-accessible surface area buried at each intermolecular interface is relatively large, ~2400 $Å^2$ total from the three individual components, which suggests a strong association. The above evidence combined with the multivalent character of interaction suggest that the contacts in the tetramer are not just mere crystal contacts.

Lengthy table referenced here

US07693698-20100406-T00001

Please refer to the end of the specification for access instructions.

Other embodiments are in the claims.

LENGTHY TABLES

The patent contains a lengthy table section. A copy of the table is available in electronic form from the USPTO web site (http://seqdata.uspto.gov/?pageRequest=docDetail&DocID=US07693698B2). An electronic copy of the table will also be available from the USPTO upon request and payment of the fee set forth in 37 CFR 1.19(b)(3).

What is claimed is:

1. A method for identifying a candidate agent that interacts with a LINGO-1 polypeptide, comprising:
  (a) generating a three-dimensional model on a computer wherein the three-dimensional model has the x-ray structural coordinates of the LINGO-1 polypeptide according to Table 2 ± a root mean square deviation from the backbone atoms that is not more than 1.5 Å;
  (b) identifying the amino acid residues forming the active site of the LINGO-1 polypeptide from the three-dimensional model in step (a) in order to generate a three-dimensional representation of the active site of the LINGO-1 polypeptide, wherein the active site of the LINGO-1 polypeptide comprises amino acids Asp13, Arg20, Arg22, Arg43, Glu60, Glu62, Leu94, Leu120, Met123, His176, Tyr142, His145, His 185, His209, His233, Ala238, Trp346, Arg347, Asn349, Asn351, Arg352, Gln353, Phe396, Arg408, Leu420, Leu426, Phe438, Asp440, Arg446, Tyr447 and Ile459 as set forth in SEQ ID NO: 1 and has the x-ray structural coordinates as shown in Table 2 ± a root mean square deviation from the backbone atoms of said amino acids of not more than 1.5 Å;
  (c) employing said three-dimensional representation from step (b) to identify a candidate agent that interacts with the active site of the LINGO-1 polypeptide; and
  (d) obtaining the candidate agent.

2. The method of claim 1, further comprising calculating a distance between an atom of the LINGO-1 polypeptide and an atom of the candidate agent.

3. The method of claim 1, further comprising altering the x-ray structural coordinates of the candidate agent.

4. The method of claim 1, further comprising detecting the ability of the candidate agent to bind to the LINGO-1 polypeptide.

5. The method of claim 1, further comprising docking a three-dimensional model of the candidate agent to the three-dimensional representation of the active site of the LINGO-1 polypeptide.

6. The method of claim 1, further comprising comparing an interaction of the candidate agent with the LINGO-1 polypeptide to an interaction of a second agent with the LINGO-1 polypeptide.

7. The method of claim 1, wherein the candidate agent is selected via computer modeling.

8. The method of claim 1, further comprising synthesizing the candidate agent.

9. The method of claim 1, further comprising detecting an ability of the candidate agent to inhibit LINGO-1 activity.

10. The method of claim 1, further comprising detecting an ability of the candidate agent to increase myelin formation in vitro or in vivo.

11. The method of claim 1, wherein the three-dimensional model comprises the structural coordinates according to Table 2 ± a root mean square deviation for alpha carbon atoms of not more than 1.0 Å.

12. The method of claim 1, wherein the three-dimensional model comprises the structural coordinates according to Table 2 ± a root mean square deviation for alpha carbon atoms of not more than 0.5 Å.

13. A method for identifying or designing a candidate agent that interacts with a LINGO-1 polypeptide, comprising:
  (a) crystallizing a LINGO-1 polypeptide comprising the amino acid sequence of SEQ ID NO:1, wherein the crystal has a space group of P2₁2₁2, unit cell dimensions of a=201.5 Å, b=149.7 Å, c=157.5 Å; and/or a crystal having a space group I222, unit cell dimensions of a=148.7 Å, b=158.6 Å, c=200.0 Å;

(b) collecting data sufficient to determine the three-dimensional structure of the LINGO-1 polypeptide from the LINGO-1 crystal;

(c) generating a three dimensional structure of the LINGO-1 polypeptide;

(d) identifying the amino acid residues forming the active side of the LINGO-1 polypeptide from the three-dimensional structure in step (c) in order to generate a three-dimensional representation of the active site of the LINGO-1 polypeptide, wherein the active site of the LINGO-1 polypeptide comprises amino acids Asp13, Arg20, Arg22, Arg43, Glu60, Glu62, Leu94, Leu120, Met123, His176, Tyr142, His145, His 185, His209, His233, Ala238, Trp346, Arg347, Asn349, Asn351, Arg352, Gln353, Phe396, Arg408, Leu420, Leu426, Phe438, Asp440, Arg446, Tyr447 and Ile459 as set forth in SEQ ID NO: 1 and has the x-ray structural coordinates as shown in Table 2 ± a root mean square deviation from the backbone atoms of said amino acids of not more than 1.5 Å; and (e) employing the three-dimensional representation from step (d) to design or select the candidate agent that interacts with the LINGO-1 polypeptide, thereby designing or identifying the agent.

14. The method of claim 13, wherein the three-dimensional structure of the LINGO-1 polypeptide comprises the x-ray structural coordinates according to Table 2 ± a root mean square deviation from the backbone atoms of the amino acids of not more than 1.0 Å.

15. The method of claim 13, wherein the three-dimensional structure of the LINGO-1 polypeptide comprises the x-ray structural coordinates according to Table 2 ± a root mean square deviation from the backbone atoms of the amino acids of not more than 0.5 Å.

16. A method for designing a candidate agent that interacts with a LINGO-1 polypeptide, comprising:

(a) generating a three-dimensional model on a computer wherein the three-dimensional model has the x-ray structural coordinates of the LINGO-1 polypeptide according to Table 2 ± a root mean square deviation from the backbone atoms that is not more than 1.5 Å;

(b) identifying the amino acid residues forming the active site of the LINGO-1 polypeptide from the three-dimensional model in step (a) in order to generate a three-dimensional representation of the active site of the LINGO-1 polypeptide, wherein the active site of the LINGO-1 polypeptide comprises amino acids Asp13, Arg20, Arg22, Arg43, Glu60, Glu62, Leu94, Leu120, Met123, His176, Tyr142, His145, His 185, His209, His233, Ala238, Trp346, Arg347, Asn349, Asn351, Arg352, Gln353, Phe396, Arg408, Leu420, Leu426, Phe438, Asp440, Arg446, Tyr447 and Ile459 as set forth in SEQ ID NO: 1 and has the x-ray structural coordinates as shown in Table 2 ± a root mean square deviation from the backbone atoms of said amino acids of not more than 1.5 Å;

(c) employing said three-dimensional representation from step (b) to design the candidate agent that interacts with the active site of the LINGO-1 polypeptide; and (d) obtaining the candidate agent.

17. The method of claim 16, wherein the three-dimensional model comprises the structural coordinates according to Table 2 ± a root mean square deviation for alpha carbon atoms of not more than 1.0 Å.

18. The method of claim 16, wherein the three-dimensional model comprises the structural coordinates according to Table 2 ± a root mean square deviation for alpha carbon atoms of not more than 0.5 Å.

19. The method of claim 16, further comprising contacting the candidate agent with the LINGO-1 polypeptide to determine the ability of the candidate agent to interact or bind to the LINGO-1 polypeptide.

20. The method of claim 19, wherein the contacting of said candidate agent with the LINGO-1 polypeptide occurs in vitro or in vivo.

21. The method of claim 16, further comprising calculating a distance between an atom of the LINGO-1 polypeptide and an atom of the candidate agent.

22. The method of claim 16, further comprising altering the structural coordinates of the candidate agent.

23. The method of claim 16, further comprising detecting the ability of the candidate agent to bind to the LINGO-1 polypeptide.

24. The method of claim 16, further comprising docking a three-dimensional model of the candidate agent to the three-dimensional model of the active site of the LINGO-1 polypeptide.

25. The method of claim 16, further comprising comparing an interaction of the candidate agent with the LINGO-1 polypeptide to an interaction of a second agent with the LINGO-1 polypeptide.

26. The method of claim 16, wherein the candidate agent is selected via computer modeling.

27. The method of claim 16, further comprising synthesizing the candidate agent.

28. The method of claim 16, further comprising detecting an ability of the candidate agent to inhibit LINGO-1 activity.

29. The method of claim 16, further comprising detecting an ability of the candidate agent to increase myelin formation in vitro or in vivo.

* * * * *